US009562809B2

(12) United States Patent
Ozawa et al.

(10) Patent No.: US 9,562,809 B2
(45) Date of Patent: Feb. 7, 2017

(54) BIOPOLYMER OPTICAL ANALYSIS DEVICE AND METHOD

(75) Inventors: Satoshi Ozawa, Musashino (JP); Takashi Anazawa, Koganei (JP); Rena Akahori, Kokubunji (JP); Satoshi Takahashi, Hitachinaka (JP); Takeshi Ohura, Kokubunji (JP); Masashi Kiguchi, Kawagoe (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/812,801

(22) PCT Filed: Jul. 21, 2011

(86) PCT No.: PCT/JP2011/066582
§ 371 (c)(1),
(2), (4) Date: Jan. 28, 2013

(87) PCT Pub. No.: WO2012/043028
PCT Pub. Date: Apr. 5, 2012

(65) Prior Publication Data
US 2013/0176563 A1    Jul. 11, 2013

(30) Foreign Application Priority Data

Sep. 29, 2010   (JP) ................. 2010-218623

(51) Int. Cl.
*G01J 3/02*   (2006.01)
*B82Y 5/00*   (2011.01)
(Continued)

(52) U.S. Cl.
CPC ............... *G01J 3/0267* (2013.01); *B82Y 5/00* (2013.01); *B82Y 15/00* (2013.01); *G01N 21/658* (2013.01); *G01N 33/48721* (2013.01)

(58) Field of Classification Search
CPC  G01N 21/65; G01N 21/658; G01N 2021/656; G01N 2021/651; G01N 2021/653; G01N 21/6458; G01N 21/6456; G01N 21/554; G01J 3/44; G01J 3/02; G01J 3/0208; G01J 3/4412; G01J 3/0205; B82Y 15/00; B82Y 30/00; B82Y 20/00; B82Y 40/00
(Continued)

(56) References Cited

U.S. PATENT DOCUMENTS 6,002,471 A * 12/1999 Quake .................... B82Y 35/00
                                                            250/458.1
6,649,894 B2   11/2003 Matsumoto et al.
(Continued)

FOREIGN PATENT DOCUMENTS

JP   2003-114184 A   4/2003
JP   2008-516237 A   5/2008
(Continued)

OTHER PUBLICATIONS

"Sub-10nm nano-gap device for single-cluster transport measurements", J. Rousseau et al., Applied Physics Letters 104, 073103 (2014).*
(Continued)

Primary Examiner — Tarifur Chowdhury
Assistant Examiner — Mohamed K Amara
(74) Attorney, Agent, or Firm — Crowell & Moring LLP

(57) ABSTRACT

The present invention provides a device and method for analyzing the characteristics of a biopolymer with excellent mechanical stability, high spatial resolution and sensitivity using a simple device construction. Specifically, the Raman scattered light of a biopolymer is measured and the properties of monomer units forming the biopolymer are analyzed by using a biopolymer property analysis chip (100a) characterized by comprising: a solid substrate (110); at least one
(Continued)

nanopore (120) disposed in the solid substrate (110); and one or more electrically conductive thin films (130a, 130b) disposed on the solid substrate (110). The biopolymer property analysis chip (100a) is characterized in that the electrically conductive thin films (130a, 130b) are disposed partially on the solid substrate (110) where the nanopore (120) is formed and a biopolymer which has penetrated into the nanopore (120) is caused to generate Raman scattered light by means of irradiation with external light.

20 Claims, 16 Drawing Sheets

(51) Int. Cl.
  *B82Y 15/00* (2011.01)
  *G01N 33/487* (2006.01)
  *G01N 21/65* (2006.01)
(58) Field of Classification Search
  USPC ............. 356/301, 73, 300, 326, 417, 451, 337,356/364, 952; 250/458.1, 459.1, 339.07, 250/339.12, 227.18; 436/171, 86
  See application file for complete search history.

(56) References Cited

U.S. PATENT DOCUMENTS

| | | |
|---|---|---|
| 6,768,556 B1 | 7/2004 | Matsumoto et al. |
| 6,949,732 B2 | 9/2005 | Kiguchi et al. |
| 8,440,403 B2* | 5/2013 | Frayling ................. 435/6.1 |
| 8,771,491 B2* | 7/2014 | Huber ..................... 204/452 |
| 2002/0182627 A1* | 12/2002 | Wang et al. ............... 435/6 |
| 2003/0066944 A1 | 4/2003 | Matsumoto et al. |
| 2003/0205552 A1* | 11/2003 | Hansford ........... B01D 67/0058 216/2 |
| 2005/0084912 A1 | 4/2005 | Poponin |
| 2007/0190543 A1* | 8/2007 | Livak ................................ 435/6 |
| 2008/0239307 A1* | 10/2008 | Talley et al. ................. 356/301 |
| 2012/0312083 A1 | 12/2012 | Akahori et al. |

FOREIGN PATENT DOCUMENTS

| | | |
|---|---|---|
| JP | 2012-26986 A | 2/2012 |
| WO | WO 2005/030997 A1 | 4/2005 |
| WO | WO 2007/011389 A2 | 1/2007 |
| WO | WO 2008/124107 A1 | 10/2008 |
| WO | WO 2009/030953 A1 | 3/2009 |
| WO | WO 2009/035647 A1 | 3/2009 |
| WO | WO 2011/121881 A1 | 10/2011 |

OTHER PUBLICATIONS

"Fabrication of sub-5 nm gaps between metallic electrodes using conventional lithographic techniques", Steinmann et al., J. Vac. Sci. Technol. B 22, 3178 (2004).*
"Plasmon resonant particles for biological detection" to D. Schultz; Current Opinion in Biotech. 2003, (14) pp. 13-22.*
Corresponding International Search Report with English Translation dated Aug. 23, 2011 (four (4) pages).
James Clarke et al., "Continuous Base Identification for Single-Molecule Nanopore DNA Sequencing", Nature Nanotechnology, 2009, pp. 1-6.
Shuai Chang et al., "Electronic Signatures of all Four DNA Nucleosides in a Tunneling Gap", Nano Letters, 2010, 1070-1075.
Elena Bailo et al., "Tip-Enhanced Raman Spectroscopy of Single RNA Strands: Towards a Novel Direct-Sequencing Method", Surface Analysis, 2008, (three (3) pages).

* cited by examiner

FIG. 5
A
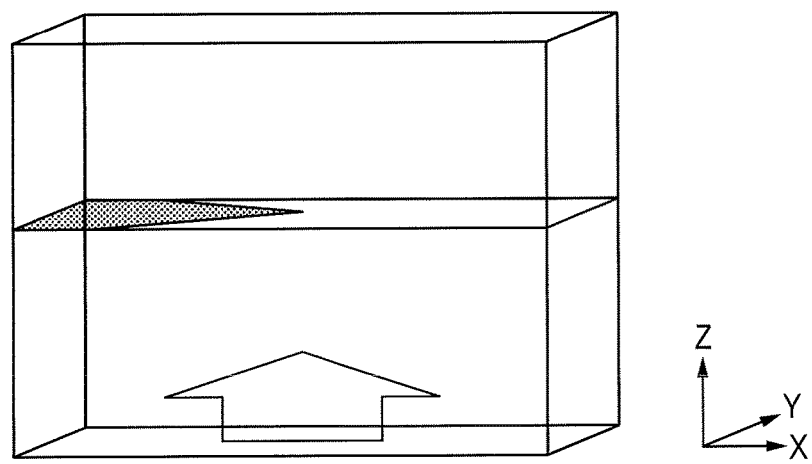
B
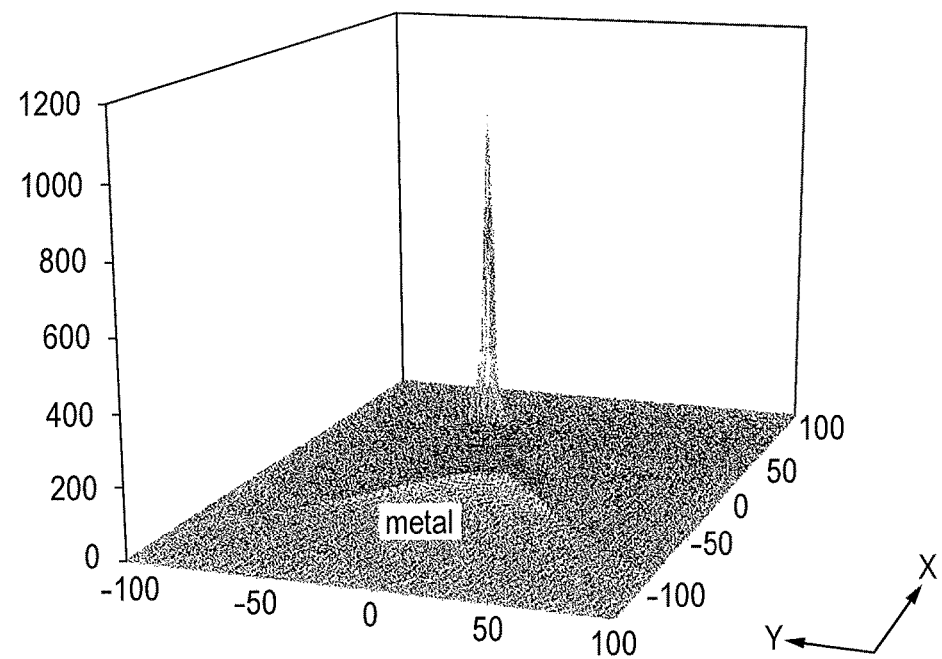

FIG. 6
A
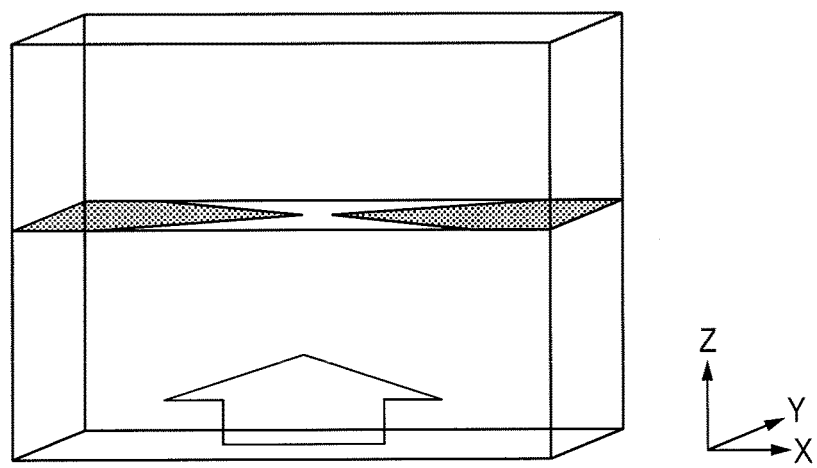
B
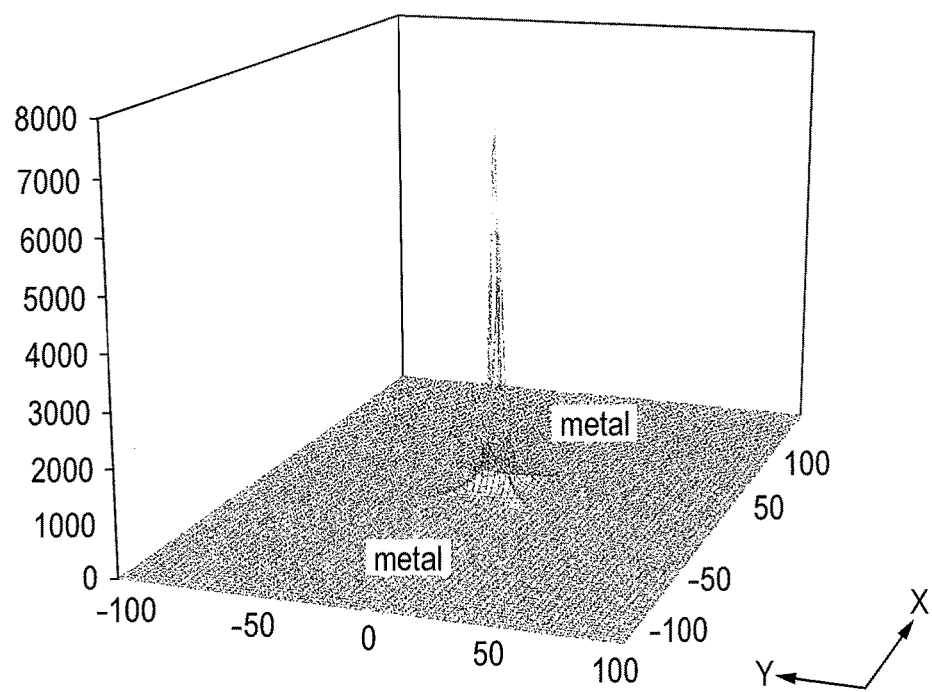

BIOPOLYMER OPTICAL ANALYSIS DEVICE AND METHOD

TECHNICAL FIELD

The present invention relates to a device and method for analyzing the characteristics of a biopolymer by using an analysis chip with a nano-sized pore (hereinafter, simply referred to as a "nanopore") formed thereon. The present invention in particular relates to a device and method for analyzing biopolymer properties characterized in that a near field is formed on the nanopore chip to detect biopolymers such as nucleic acid optically without the need for labeling.

BACKGROUND ART

Techniques using nanopores attract tremendous attentions as an approach to the implementation of post-Next-Generation DNA sequencers. It is considered that the nanopore techniques have a noteworthy advantage in that they allow the characteristics of a biopolymer to be analyzed without DNA labeling, namely using no reagents, such as an enzyme and fluorescent dye. The nanopores may be largely classified into two types. One is a so-called bionanopore, of which channel protein forming a nano-sized aperture (hereinafter, simply referred to as a "nanopore") is laid inside a bilayer membrane, and another is a so-called solid state nanopore, which is made by microfabricating a semiconductor material.

Two types of DNA analytical methods using these nanopores have been proposed. The first one is a current blockade method. Specifically, ionic current flows through the nanopore when voltage is applied between electrodes, each of which is disposed with electrolyte solution in each of reservoirs for solution installed on the both sides of a thin film with the nanopore formed thereon. The magnitude of the ionic current is proportional to the cross sectional area of the nanopore in terms of the first approximation. When DNA passes through the nanopore, it blocks the nanopore and reduces its effective cross-sectional area, resulting in a reduction of ionic current. The amount of the reduction of ionic current is called current blockade. A difference between a single stranded DNA and a double stranded DNA may be discriminated based on the magnitude of the current blockade. Moreover, it has been reported that one form of nanopore enables the types of DNA bases to be discriminated based on the magnitude of the current blockade (Nonpatent Literature 1, hereinafter also simply referred to as a "first example, according to prior art"). However, it is considered that since the bilayer membrane used for the biopore is a fragile thin film made of weakly-associated low molecular organic compounds, it has a problem of mechanical instability. Moreover, since the process of integrating channel protein inside the bilayer membrane relies on a natural phenomenon, the bilayer membrane has a problem with control of the number of channels and reproducibility. In contrast, it is considered that a solid state nanopore, under which thin film is formed of a semiconductor substrate, or the like, is advantageous in structural stability over a bionanopore. Since the nanopore is mechanically formed, it has another advantage. Furthermore, a device and method for analyzing biomolecules passing through a solid state nanopore formed on a thin film made of graphene instead of the semiconductor substrate have been reported (Patent Document 1). However, identification of the types of DNA bases using the nanopore by means of current blockade has not been reported.

The second one is a tunneling current method. Specifically, the method has been proposed, which is characterized in that a pair of electrodes are disposed facing to each other on the nanopore wall; voltage is applied between the electrodes; DNA passing through the nanopore and tunneling current between the electrodes are measured; and the DNA is analyzed based on the magnitude of the tunneling current. Such a related technique has been reported that when a nucleoside with modified sugar is dissolved in an organic solvent and introduced between nanogap electrodes, and then the tunneling current is measured using a scanning probe microscope, the average of tunneling current values depends on the types of the bases (Nonpatent Document 2, hereinafter, also simply referred to as a "second example, according to prior art"). However, the second example has limitations on experimental conditions because the sample is a nucleoside (containing no phosphoric acid) but not a chained nucleic acid; the sample needs to be modified; the sample needs to be dissolved in an organic solvent; and no nanopore is used, as well as has a problem of low ability to identify bases because the tunneling current has a distribution and partially overlapped between different types of bases.

Other methods for determining base sequences using the nanopore or similar structure have been reported including such methods that a nucleotide (monomer) is separated from a chained nucleic acid (polymer) with an enzyme and caused to pass through a nanochannel or microchannel filled with an aggregate (100 nm to 200 nm in size), for example, an aggregate of silver particulates, and then the nucleotide is identified on the surface of the silver-particulate aggregate by Surface Enhanced Raman Scattering (Patent Document 2); and that an enzyme or the like is filled inside the nanopore to be caused to interact with the nucleotide in a DNA sequence, the resulting bond is controlled using the nanopore, and the nucleotide is determined (Patent Document 3). Any of the aforementioned methods needs to use agents, such as an enzyme, and has complicated device construction and processes.

On the other hand, TERS (Tip Enhanced Raman Scattering) has been reported as another approach to the measurement of a single molecular nucleic acid without labeling (Nonpatent Document 3, hereinafter, also simply referred to as a "third example, according to prior art"). According to this method, a silver tip is formed on the tip of an AFM (Atomic Force Microscope) probe; the chained nucleic acid molecule immobilized on a mica substrate is scanned by AFM to take an AFM image of the nucleic acid molecule; the probe is caused to have access to the nucleic acid; and a laser beam is irradiated thereon. Then, a local near field is formed at the probe tip and caused to excite the nucleic acid. The Raman scattered light emitted by the excited nucleic acid is spectroscopically measured to obtain the Raman scattering spectrum of the nucleic acid. Since the S/N ratio of the resulting signal is larger than the number of the bases contained in the nucleic acid, such sensitivity that enables monobasic measurement, is achieved. This method has an advantage in that since the Raman scattering spectrum provides two-dimensional information of a wavenumber vs. intensity pattern, the information volume thereof is exponentially larger than that of one-dimensional information provided by current blockade or tunneling current, exhibiting high ability to identify the bases in qualitative analysis. The size of the near field depends on the curvature of the probe tip and the spatial resolution according to the third example is about 10 nm. Since this value is equivalent to about 30 bases in terms of the number of the bases contained in a nucleic acid, the result obtained in this way contains overlapped information for a multiple of bases. To determine the information for the individual bases from the overlapped information, such a method, for example, has been proposed that a step of scanning along the chain of the nucleic acid with a probe and a step of inferring the bases entering and going out from the near field based on a variance (difference) in spectrum are repeated to obtain sequence information (hereinafter, simply referred to as a "difference method"). To implement this method, it is required that: the nucleic acid is immobilized on the solid state substrate in advance; a high resolution AFM device including high precision stage for measurement is installed; and such a delicate operation that an AFM probe is three-dimensionally scanned at the precision of sub-nm is performed. In other words, the second method has a problem of complicated device construction and operation.

CITATION LIST

Patent Literature

Patent Literature 1: WO2009/035647
Patent Literature 2: WO2005/030997
Patent Literature 3: WO2008/124107

Nonpatent Literature

Nonpatent Literature 1: Clarke, J. et al., Nat. Nanotech. (2009), vol. 4, pp. 265-270.
Nonpatent Literatute 2: Chang, S. et al., Nano Lett. (2010), vol. 10, pp. 1070-1075.
Nonpatent Literature 3: Bailo, E. et al., Angew. Chem. Int. Ed. (2008), vol. 47, pp. 1658-1661.

SUMMARY OF INVENTION

Technical Problem

The method (the first example, according to prior art) for analyzing a biopolymer using a biopore by means of current blockade with low mechanical stability is difficult to obtain reproducible result stably. Moreover, the method for analyzing a biopolymer using the nanopore by means of tunneling current (the second example, according to prior art), which has low ability to identify bases, is difficult to read out the base sequence of nucleic acid at high precision. The method for analyzing a biopolymer (the third example, according to prior art) using TERS, which has complicated device construction, needs to be operated carefully.

Thus, an object of the present invention is to provide a device and method for analyzing the characteristics of a biopolymer with excellent mechanical stability, high spatial resolution and sensitivity using a simple device construction.

Solution to Problem

Through their earnest investigation to solve the aforementioned problems, the inventers of the present invention succeeded in improving spatial resolution and sensitivity when the characteristics of the biopolymer penetrating into the solid state nanopore was analyzed based on the Raman scattered light by disposing appropriate electroconductive thin films on a substrate in correct positions. In other words, the present invention includes the following members and steps.

[1] A biopolymer property analysis chip, characterized by having:
a solid state substrate;
at least one nanopore disposed in the solid state substrate; and
at least one electroconductive thin film disposed on the solid state substrate, and also characterized in that the electroconductive thin films are disposed partially on the solid state substrate where the nanopore is formed, and a biopolymer which has penetrated into the nanopore is caused to generate a Raman scattered light by means of irradiation with external light.

[2] The biopolymer property analysis chip defined in [1], and characterized in that the electroconductive thin films are caused to generate a near field at the edges thereof facing the opening of the nanopore, which in turn causes the biopolymer, which has penetrated into the nanopore, to generate Raman scattered light by means of irradiation with the external light on the electroconductive thin films.

[3] The biopolymer property analysis chip defined in [1] or [2], and characterized in that the electroconductive thin films have acute-angled edges, which are disposed facing the opening of the nanopore.

[4] The biopolymer property analysis chip defined in any one of [1] to [3], and characterized in that at least the two electroconductive thin films are formed and disposed so as to sandwich the opening of the nanopore facing to each other.

[5] The biopolymer property analysis chip defined in any one of [1] to [4], and characterized in that the electroconductive thin films are made of metal.

[6] The biopolymer property analysis chip defined in any one of [1] to [4], and characterized in that the electroconductive thin films are made of graphite.

[7] The biopolymer property analysis chip defined in any one of [1] to [6], characterized in that the thickness of the electroconductive thin films is 0.1 to 10 nm.

[8] The biopolymer property analysis chip defined in any one of [1] to [7], and characterized in that the solid state substrate has a thin film part substantially capable of transmitting light where the nanopore is disposed.

[9] The biopolymer property analysis chip defined in any one of [1] to [8], and characterized in that the electroconductive thin films are disposed on the surface of the solid state substrate.

[10] The biopolymer property analysis chip defined in any one of [1] to [8], and characterized in that the electroconductive thin films are disposed at the middle depth of the nanopore of the solid state substrate along the central axis thereof.

[11] The biopolymer property analysis chip defined in any one of [1] to [10], and characterized in that the depth of the nanopore is larger than or equal to three times that of monomer units building up the biopolymer.

[12] The biopolymer property analysis chip defined in any one of [1] to [11], and characterized in that the biopolymer is selected from the group of nucleic acid, peptide nucleic acid, protein, sugar chain, and aptamer.

[13] The biopolymer property analysis chip defined in any one of [1] to [12], and characterized in that the biopolymer property analysis is to determine the base sequence of a nucleic acid.

[14] A biopolymer property analysis device characterized by having:
the biopolymer property analysis chip defined in any of [1] to [13];
a light source; and a one-dimensional or two-dimensional detector with frame rate of 1 kHz or higher, and characterized in that a Raman scattered light generated by a biopolymer is detected on the analysis chip using the detector by means of irradiation with external light on the analysis chip.

[15] The biopolymer property analysis chip defined in [14], and characterized in that frame buffer memory for recording measured values read out from the detector is further included.

[16] The biopolymer property analysis chip defined in [14] or [15], and characterized in that a photoelectron intensifier means is included as the detector.

[17] The biopolymer property analysis chip defined in any one of [14] to [16], and characterized in that a means for driving the sample, which causes the monomers in the biopolymer to penetrate into the nanopore one by one, is further included.

[18] A method for analyzing biopolymer properties characterized by including the steps of:
  causing the biopolymer, which has penetrated into a nanopore, to generate a Raman scattered light by means of irradiation with external light on the biopolymer property analysis chip defined in any one of [1] to [13] and
  analyzing the characteristics of the biopolymer based on the Raman scattering spectrum.

[19] The method for analyzing the characteristics of the biopolymer defined in [18], and characterized in that the biopolymer is selected from the group of nucleic acid, peptide nucleic acid, protein, sugar chain, and aptamer.

[20] The method for analyzing the characteristics of the biopolymer defined in [18] or [19], and characterized in that the base sequence of the nucleic acid is determined.

[21] The method for analyzing biopolymer properties defined in [18] to [20], and characterized in that the biopolymer is contained in a sample solution containing a second polymer, which is incapable of penetrating into the nanopore.

Advantageous Effects of Invention

The present invention provides a biopolymer property analysis chip. The property analysis chip of the present invention using a solid state nanopore method has advantageous in that it has high constructive stability and reliability compared with a bionanopore-based chip using a bilayer membrane method.

The analysis chip of the present invention analyses a biopolymer using the Raman scattering spectrum as an indicator to determine the types of the monomers contained in the biopolymer. The spectrum having two-dimensional information, namely a wavenumber or wavelength-intensity pattern, contains an exponentially large volume of information and has a high ability of identify bases in qualitative analysis, compared with one-dimensional information, for example, tunneling current intensity. Accordingly, the present invention has an extremely higher ability to identify bases than that of the nanopore by means of tunneling current.

Moreover, the property analysis chip with multinanopore of the present invention is capable of analyzing a plurality of biopolymers concurrently in parallel using a spectrooptics, which measures a plurality of spectra in parallel. For this reason, the property analysis chip with multinanopore of the present invention achieved high throughput compared with analysis devices and methods according to prior art.

Furthermore, the present invention provides a biopolymer property analysis device and method. The property analysis device of the present invention is capable of controlling the speed at which the biopolymer penetrates into the nanopore, and eliminating the need for a step of immobilizing the biopolymer to be analyzed on the solid state substrate in advance and the need for a complicated device, for example, a high-resolution high precision stage or Atomic Force Microscope (AFM). In addition, the need for a delicate step of causing the AFM probe to scan two-dimensionally at the accuracy of sub-nm, is eliminated. For this reason, the device construction and operation of the property analysis device of the present invention is simpler than those in analysis using the TERS method according to prior art.

BRIEF DESCRIPTION OF DRAWINGS

FIG. 5A is a schematic diagram showing the structure of a triangle-shaped metal thin film with an acute angle and FIG. 5B is a view showing the result of simulation of a near field generated in the vicinity of the metal thin film.

FIG. 6A is a schematic diagram showing the structures of two triangle-shaped metal thin films and FIG. 6B is a view showing the result of simulation of a near field generated in the vicinity of the metal thin films.

DESCRIPTION OF EMBODIMENTS

Figure 1:
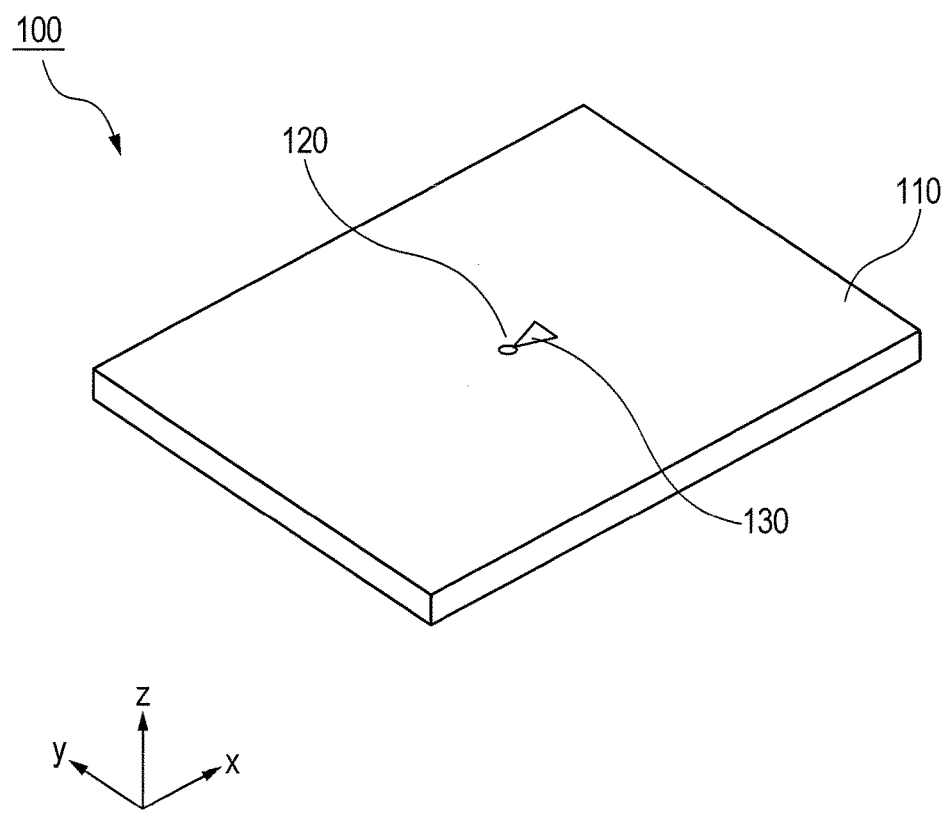
FIG. 1 is a schematic diagram of a nanopore chip for analyzing the characteristics of a biopolymer.

Hereinafter, the present invention will be described in detail. This application claims priority based on Japanese Patent Application No. 2010-218623 filed on Sep. 29, 2010 and integrates the contents described in the Description and/or Drawings of the aforementioned patent application cited herein by reference.

The present invention relates to a device for analyzing the characteristics of a biopolymer using a nanopore and a Raman scattered light (preferably Tip Enhanced Raman Scattering (TERS)) (hereinafter, simply referred to as a "biopolymer property analysis chip" or "analysis chip of the present invention"), and a biopolymer property analysis device with the device and a method for analyzing the characteristics of the biopolymer. Accordingly, the biopolymer property analysis chip of the present invention has a solid state substrate, at least one nanopore disposed in the solid state substrate, and at least one electroconductive thin film disposed partially at the nanopore of the solid state substrate.

The solid state substrate may be made of any of electric insulator materials, for example, an inorganic or organic material (including polymeric material). The electric insulator material is exemplified by silicon, glass, quartz, polydimethylsiloxane (PDMS), polytetrafluoroethylene (PTFE), polystyrene, and polypropylene. The size and thickness of the solid state substrate include, but are not limited to those allowing the nanopore to be disposed and are adjusted so as to be caused the solid state substrate to fit into the components (such as a detector) of an analysis device used in analyzing the biopolymer described later. The solid state substrate may be fabricated by a method known in the art, or a commercially-available solid state substrate may be acquired. The solid state substrate can be fabricated using any of techniques such as photolithography and etching; laser abrasion; injection molding; casting; molecular beam epitaxy; chemical vapor deposition (CVD); electron beam; and focused ion beam. The solid state substrate may be coated to avoid the adsorption of other molecules on the surface thereof.

The solid state substrate has preferably a thin film part where a nanopore is disposed. Specifically, the nanopore can be easily and efficiently formed on the solid state substrate by disposing the thin film part made of material and having thickness, which are appropriate for forming the nano-sized pore on the solid state substrate. This thin film part may be made of the same material as that of the solid state substrate, or may be made of another electric insulator material. In terms of forming the nanopore, the material for the thin film is preferably, for example, silicon oxide ($SiO_2$); silicon nitride (SiN); silicon oxynitride (SiON); metal oxide; or metal silicate. Moreover, in terms of excitation efficiency and condensation efficiency of external light described later, preferably the thin film part (and the entire solid state substrate in some cases) is substantially transparent. The term "substantially transparent" used herein means that the external light is transmitted by about 50% or more, preferably 80% or more. The thin film part may be either a monolayer or a multilayer, and if it is a multilayer, the electroconductive thin film described later may be disposed between the layers of thin film parts. The thickness of the solid state substrate is 10 to 200 nm, preferably 15 to 100 nm, more preferably 20 to 50 nm. The thin film part can be formed on the solid state substrate by a technique known in the art, for example, low pressure chemical vapor deposition (LPCVD).

At least one nanopore may be disposed in the solid state substrate. The terms "nanopore" and "pore" used herein mean a nanometer (nm)-sized pore, which penetrates through the solid state substrate, preferably the thin film part on the solid state substrate. In other words, the analysis chip of the present invention is classified as a so-called solid state nanopore. The term "aperture" used herein means the part of the pore opened on the surface of the solid state substrate. The biopolymer and ions contained in a sample solution penetrate into the nanopore from the aperture and go out from the nanopore from the same aperture or an aperture on the opposite side.

The size of the pore (the size of the aperture) appropriate for the type of a biopolymer to be analyzed can be selected from, for example, 1 to 100 nm, preferably 1 to 50 nm; specifically larger than or equal to 1 nm and smaller than or equal to 2 nm, larger than or equal to 3 nm and smaller than or equal to 5 nm, larger than or equal to 10 and smaller than or equal to 50 nm, or the like. The diameter of ssDNA (single stranded DNA) is about 1.5 nm, and the range of pore diameter appropriate for analyzing ssDNA is about 1.5 to 10 nm, preferably about 1.5 to 2.5 nm. The diameter of dsDNA (double stranded DNA) is about 2.6 nm, and the range of pore diameter appropriate for analyzing dsDNA is about 3 to 10 nm, preferably 3 to 5 nm. Similarly, the pore size can be selected depending on the outer dimension of the biopolymer in the case of other biopolymers, for example, protein, sugar chain, or the like. The depth of the nanopore can be adjusted by adjusting the thickness of the solid state substrate or the thin film part thereof. The depth of the nanopore is more than two times that of monomer units building up the biopolymer, preferably more than three times, more preferably more than five times. If a nucleic acid is selected as a biopolymer, the depth of the nanopore is preferably larger than or equal to three bases in length, for example, about 1 nm. This allows the biopolymer to penetrate into the nanopore while its shape and moving speed is being controlled, achieving highly-sensitive and highly-accurate analysis. The shape of the pore is basically cylindrical but may be elliptical or polygonal.

At least one pore can be disposed in the solid state substrate, and if a plurality of pores is disposed, preferably they are regularly aligned. The pore can be formed in the solid state substrate by a method known in the art, for example, by means of irradiation with electron beam from a transmission electron microscope (TEM) or using nanolithography or ion beam lithography.

At least one electroconductive thin film is disposed partially on the solid state substrate where the nanopore is formed. The electroconductive thin film comes into contact only with a part of the circumference of the nanopore but not with the entire circumference for the reason described later. The electroconductive thin film can be made of a material with electroconductivity or light scattering property. Such a material is exemplified by metals, for example, a platinum group such as platinum, palladium, rhodium, and ruthenium; gold, silver, copper, aluminum, nickel; and graphite, for example, graphene (may be either a monolayer or a multilayer).

As known from the definition of the thin film, the electroconductive thin film is formed into a flat-shape. The thickness of the electroconductive thin film is 0.1 to 10 nm, preferably 0.1 to 7 nm, depending on the material to be used. With thinner electroconductive thin film, the near field to be generated can be limited, allowing high-resolution and high-sensitivity analysis. Moreover, the size of the electroconductive thin film is not, in particular, limited and can be selected appropriately depending on the sizes of the solid state substrate and the nanopore, and on the wavelength of excitation light to be used. It should be noted that if the electroconductive thin film is not flat-shaped but has a curvature or the like, the near field is induced at the curvature portion, causing light energy to leak out and a Raman scattered light to generate at an unintended point. In other words, a background light is magnified and the S/N ratio is reduced. For this reason, the electroconductive thin film is preferably flat-shaped, namely the cross sectional shape thereof is preferably linear with no curvature. The flat-shaped electroconductive thin film is not only effective in reducing the background light and increasing the S/N ratio but also preferable in terms of uniformity of the thin film and reproducibility in fabricating the thin film.

The electroconductive thin film can be formed into any shape, which allows the near field to be generated and magnified by means of irradiation with external light. The probes, which generate this near field, are known in the art and for example, those formed into a shape with an acute-angled edge or metallic bow-tie structure, which causes the near field to be generated and amplified in the case of Tip Enhanced Raman Scattering (TERS), are known.

A preferable flat shape of the electroconductive thin film is exemplified by a shape with an acute-angled edge and it is, in particular, preferable to dispose this edge so as to face the nanopore. In this case, the angle of the edge is 10 to 80 degrees, preferably 20 to 60 degrees, more preferably 20 to 40 degrees. For more information for the preferable shape of the electroconductive thin film (light scattering substance), for example, refer to Japanese Unexamined Patent Application Publication No. 2009-150899. The vertex of the edge of the electroconductive thin film may not be shaped into a strict point, and may be rounded with a curvature smaller than a certain size or preferably smaller than or equal to 10 nm in radius. As the shape of the electroconductive thin film other than the acute-angled edge facing the nanopore, an angle more obtuse than the angle of the vertex of the edge can be used. Since the near field is induced at the angle portion, from which light energy leaks out, it is preferable that complicated shapes are avoided as much as possible and a round-shape without angle or linear shape is preferably used for the edges other than the acute-angled edge facing the nanopore. The electroconductive thin film as a whole can be formed into any shape as long as it has an acute-angled edge facing the nanopore, for example, any of polygons including triangle, tetragon, and pentagon; sector; and mixture of round and triangle.

On the other hand, the metallic bow-tie structure can be also used for the shape of the electroconductive thin film. In other words, two electroconductive thin films which are round-shaped, ellipse-shaped, or polygon-shaped are disposed such that the convexes of the shapes thereof face to each other. For more information for this metallic bow-tie structure, for example, refer to U.S. Pat. No. 6,649,894. The metallic bow-tie structure can be considered to be a structure with a gap (aperture) inserted in a region where the near field is formed. Insertion of the gap brings anisotropy, improving detection sensitivity. For more information for this technique, for example, refer to U.S. Pat. No. 6,768,556 and U.S. Pat. No. 6,949,732.

At least a part of the electroconductive thin film is disposed facing the nanopore, and preferably, with the thin film, structures such as the edge for generating the near field is disposed facing the nanopore. The electroconductive thin film may be disposed on the surface of the solid state substrate, or may be disposed between the solid state substrates as long as at least a part, preferably, in particular, the edge is disposed facing the nanopore. Giving an example, the electroconductive thin film may be disposed on the surface of the solid state substrate so as to face the opening of the nanopore. Alternatively, the electroconductive thin film may be disposed at the almost middle depth of the nanopore on the solid state substrate along the central axis thereof. In this case, the electroconductive thin film is preferably structured so as to be disposed between the thin films on the solid state substrate. Since this forms the near field in the vicinity of the middle point of the nanopore along the central axis thereof (in the direction of depth), the biopolymer can be caused to generate a Raman scattered light inside the nanopore while the shape and moving speed of the biopolymer is being controlled, allowing high-accuracy and high sensitivity analysis. Preferably, the direction of polarization of an external light to be irradiated is taken into account when the electroconductive thin film is disposed on the solid state substrate.

At least one electroconductive thin film may be disposed so as to face each of the nanopores, but the number of the thin film is not limited to an odd number but can be an even number. Giving an example, one, two, three, four, or more electroconductive thin films can be disposed so as to face each of the nanopores. As in the case of the embodiments described later, since a strong light field is formed with a plurality of electroconductive thin films, two or more electroconductive thin films are preferably disposed so as to face each of the nanopores. Alternatively, the electroconductive thin film can be formed into one thin film with a plurality of units, assuming that the aforementioned shape is one unit. Specifically, the electroconductive thin film can be formed into a thin film structure coupling two units as described in an embodiment 5.

Then, considerations to be taken in disposing a plurality of electroconductive thin films will be described. To dispose a plurality of electroconductive thin films coupling to each other, at least a part, preferably, in particular, the part facing the nanopore of the entire shape formed by the coupled electroconductive thin films needs to have an acute-angled edge. When the plurality of electroconductive thin films are coupled to each other in the vicinity of the nanopore, this acute-angled edge may be lost; however, since the edge is requisite for efficient formation of the near field, loss of the edge must be avoided. In this context, when one electroconductive thin film is used, the same malfunction as aforementioned may occur if it is disposed so as to surround the circumference of the nanopore. Specifically, a malfunction may occur that a charge induced on the electroconductive thin film by means of irradiation with excitation light passes around the nanopore through the electroconductive thin film surrounding the nanopore, preventing a dipole from being formed in the nanopore. For the reason described above, at least one electroconductive thin film on the biopolymer property analysis chip of the present invention needs to be disposed only partially around the circumference of the nanopore at the solid state substrate, but not on the entire circumference of the nanopore.

The electroconductive thin film is preferably disposed such that the edge thereof faces the opening of the nanopore. More specifically, the electroconductive thin film is disposed on the surface perpendicular to the central axis of the nanopore with the edge of the thin film facing the opening of the nanopore. To dispose at least two electroconductive thin films, these electroconductive thin films are preferably disposed so as to sandwich the opening of the nanopore facing each other. In this case, the biopolymer, which has penetrated into the nanopore, is caused to generate a Raman scattered light by means of the near field generated at the edge where the electroconductive thin films face the nanopore, which in turn is induced by the irradiation with an external light on the electroconductive thin films.

The electroconductive thin films can be fabricated in a manner known in the art to dispose on the solid state substrate. Giving an example, the electroconductive thin film made of silver can be formed into a desired shape by means of irradiation with electron beam after a silver thin film with desired thickness has been formed on the substrate by sputtering. To make the electroconductive thin film of a graphene made of graphite can be mounted on a support substrate and formed into a desired shape by means of irradiation thereon with electron beam.

The biopolymer, which has penetrated into the nanopore, is excited to generate a Raman scattered light by means of irradiation on the analysis chip of the present invention with an external light, and based on the generated Raman scattering spectrum, the characteristics of the biopolymer can be analyzed. Preferably, the biopolymer is two-dimensionally scanned with light irradiated from a near field, which has been formed at the edge facing the opening of the nanopore by the electroconductive thin film of the present invention by means of irradiation thereon with an external light. The thickness of the formed near field is basically equal to that of the electroconductive thin film; namely, the thickness of the electroconductive thin film, which is formed perpendicular to the central axis of the nanopore, is equal to that of the electroconductive thin film in the direction of the central axis of the formed near field. For this reason, the use of the analysis chip of the present invention allows the biopolymer to be analyzed at high spatial resolution and high sensitivity.

Moreover, the present invention also relates to a biopolymer property analysis device having the aforementioned analysis chip of the present invention (hereinafter, simply referred to as the "analysis device of the present invention"). Accordingly, the analysis device of the present invention has the aforementioned analysis chip, a light source, and a one- or two-dimensional detector with frame rate of higher than or equal to 1 kHz. In the analysis device of the present invention, an external light is irradiated on the analysis chip of the present invention from the light source, and the Raman scattered light generated by the biopolymer in the analysis chip is detected using the detector.

A light source known in the art, which irradiates an external light (excitation light) with wavelength capable of generating a Raman scattered light, can be used as a light source. For example, the allowed light source includes but not limited to krypton (Kr) ion laser; neodymium (Nd) laser; argon (Ar) ion laser; YAG laser; nitrogen laser; and sapphire laser, which irradiate an external light with wavelength of in the range of 400 to 800 nm, preferably 500 to 600 nm. Moreover, it is preferable that a confocal lens and an objective lens are used with the light source to irradiate and condense the external light on the analysis chip from the light source. To reduce a background signal, a filter, a half mirror, or confocal pin holes may be used with the light source. The construction of the device for detecting the Raman scattered light is known in the art, and those skilled in the art can select preferable components if appropriate.

A Raman scattered light may be generated by normal Raman scattering, resonance Raman scattering, Tip Enhanced Raman Scattering (TERS), Surface Enhanced Raman scattering (SERS), or the like.

Any spectroscopic detector with frame rate (moving speed) higher than or equal to 1 kHz and capable of detecting a Raman scattered light can be used as a detector. One or more one- or two-dimensional detectors can be used depending on the number and disposition of the nanopores in the analysis chip to be used. This type of spectroscopic detector includes a CCD (charge-coupled device) image sensor, CMOS (complementary metal oxide semiconductor) image sensor, and other types of high sensitivity element (for example, avalanche photodiode) image sensors. The detector preferably has a photointensifier means, for example, an image intensifier to prevent the sensitivity of the detector from deteriorating associated with speeding-up of detection.

Moreover, the detector preferably has large-capacity memory capable of directly recording the image information for the Raman scattered light, allowing high-speed analysis without the need for the use of cables, a board, a computer, or the like. Giving an example, the analysis device of the present invention preferably further has frame buffer memory for recording measured values read out from the detector. Furthermore, the analysis device of the present invention may be interfaced to an output device (for example, a computer) for digitizing and outputting the measured values read out from the detector.

In addition, the analysis device of the present invention preferably has a mechanism for controlling the moving speed of the biopolymer, namely a means for transferring the sample. The means for transferring the sample causes the monomers in the biopolymer to penetrate into the nanopore in the analysis chip one by one in synchronization with, for example, the frame rate of the detector. An instrument (function generator, electrode, etc.) for driving the sample for driving the biopolymer by means of electrophoresis, for example, can be used as this type of means. This instrument for driving the sample allows the movement of the biopolymer to be controlled such that the monomers in the biopolymer to sequentially penetrate into and migrate from the nanopore to obtain the Raman scattering spectrum corresponding to each of monomers (constitutional units) over time.

To control the moving speed of the biopolymer, a method for increasing the viscosity of a sample solution containing the biopolymer may be used. Giving an example, the Brownian motion of the biopolymer can be suppressed by controlling the temperature in the vicinity of the analysis chip so as to drop the temperature of the sample solution and increase the viscosity of the sample solution. Alternatively, the addition of a second polymer to be not measured in the sample solution not only increases the viscosity of the sample solution but also makes the conformation of the biopolymer into linear shape, allowing the shape and moving speed of the biopolymer to be controlled. In this case, the use of preferably a polymer of which internal diameter is larger than that of the nanopore, more preferably a polymer that is three-dimensionally-crosslinked as the second polymer prevents the second polymer from penetrating into the nanopore, enabling the Raman scattered light from the second polymer, which is not to be measured, to be eliminated.

Another, method for controlling the moving speed of the biopolymer is to apply differential pressure to the sample solutions contained in the upper part and lower part of the analysis chip of the present invention. Applying a force opposite to the force exerted when the biopolymer passes through the nanopore by means of electrophoresis can reduce the speed at which the biopolymer passes through the nanopore.

When the biopolymer is caused to penetrate into the nanopore while the shape and moving speed thereof is being controlled, the main axis of the biopolymer and the central axis of the nanopore are almost coincident with each other. The biopolymer, when driven by the means for transferring the sample, passes through the nanopore, and the unit elements (monomers) of the biopolymer pass sequentially through the near field formed on the analysis device. Specifically, the monomers aligned along the main axis of the polymer are sequentially exposed to the near field, and generate Raman scattered lights. These Raman scattered lights are measured using the detector to obtain sequentially the spectra of Raman scattered lights derived from the monomers.

In the present invention, the characteristics of the biopolymer can be analyzed using the aforementioned biopolymer property analysis chip or property analysis device of the present invention. The term "biopolymer" used herein means an oligomer or polymers composed of a plurality of low molecules, namely, unit structures (monomers) coupled to each other or those contained in living organisms or induced from those contained in living organisms. Specifically, the biopolymer includes nucleic acids, for example, single stranded DNA (ssDNA) and double stranded DNA (dsDNA); single stranded RNA (ssRNA) and double stranded RNA (dsRNA), hybrid nucleic acids composed of DNA and RNA; peptide nucleic acid; protein and peptide, for example, protein and peptide composed of D- and L-amino acids; sugar chains, for example, polysaccharide and sugar chains contained in glycoprotein; and aptamer, for example, RNA aptamer. It should be noted that the biopolymer includes polymers containing base sequences and unit elements, which are not seen in the natural world, for example, artificially-synthesized polymer molecules having base sequences such as poly(A), poly(T), poly(G), and poly(C) or arbitrary sequences. Moreover, the biopolymer includes a nucleic acid prepared by a nucleic acid amplification technique (for example, polymerase chain reaction) known in the art, and a nucleic acid cloned into a vector. The methods for preparing samples containing these types of biopolymers are known in the art, and those skilled in the art can select any of methods for preparing samples depending on the types of biopolymers if appropriate.

The term "analysis" used herein means biopolymer property analysis. The term "analysis" used in preferred embodiment means to analyze the sequence of monomers, which are units building up a biopolymer, for example, to analyze the base sequence of nucleic acid. To analyze the characteristics of the biopolymer, the optical spectrum for each of monomers (bases when the biopolymer is nucleic acid) building up the biopolymer is measured and qualitative analysis (identification) of the monomers is performed based on the comparison with the wavenumber or wavelength (hereinafter, also simply referred to as "specific band") at which the spectrum shows its peak. Accordingly, in the present invention, the Raman scattered light derived from each of monomers building up the biopolymer is obtained sequentially; the obtained Raman scattering spectra are compared with a standard spectrum; the characteristics (namely, types) of monomers are determined; and these steps are sequentially executed over time, allowing the sequence of the monomers aligned in the biopolymer to be determined, namely, sequence analysis to be performed.

EMBODIMENTS

Hereinafter, the present invention will be described in detail. It should be noted that the embodiments described below do not limit the present invention.

First Embodiment

Nanopore Chip and Biopolymer Property Analysis Using it

An example of the construction of a nanopore chip for analyzing the characteristics of a biopolymer of the present invention will be described referring to FIG. 1. FIG. 1 is a schematic diagram of a nanopore chip 100 for analyzing the characteristics of a biopolymer according to this embodiment of the present invention. As shown in the figure, the nanopore chip 100 is composed a substrate 110, a nanopore 120, and an electroconductive thin film 130, or the like. As shown in FIG. 1, a plane parallel to a widest plane (hereinafter, simply referred to as a substrate surface) of the substrate 110 is defined as a x-y plane, a direction, in which an electroconductive thin film 130 and the nanopore 120 are aligned, is defined as a x axis, and a direction perpendicular to the x-y plane is defined as a z axis. The nanopore 120 is formed approximately perpendicularly to the substrate surface; namely, the central axis of the nanopore is parallel with the z axis.

Figure 2:
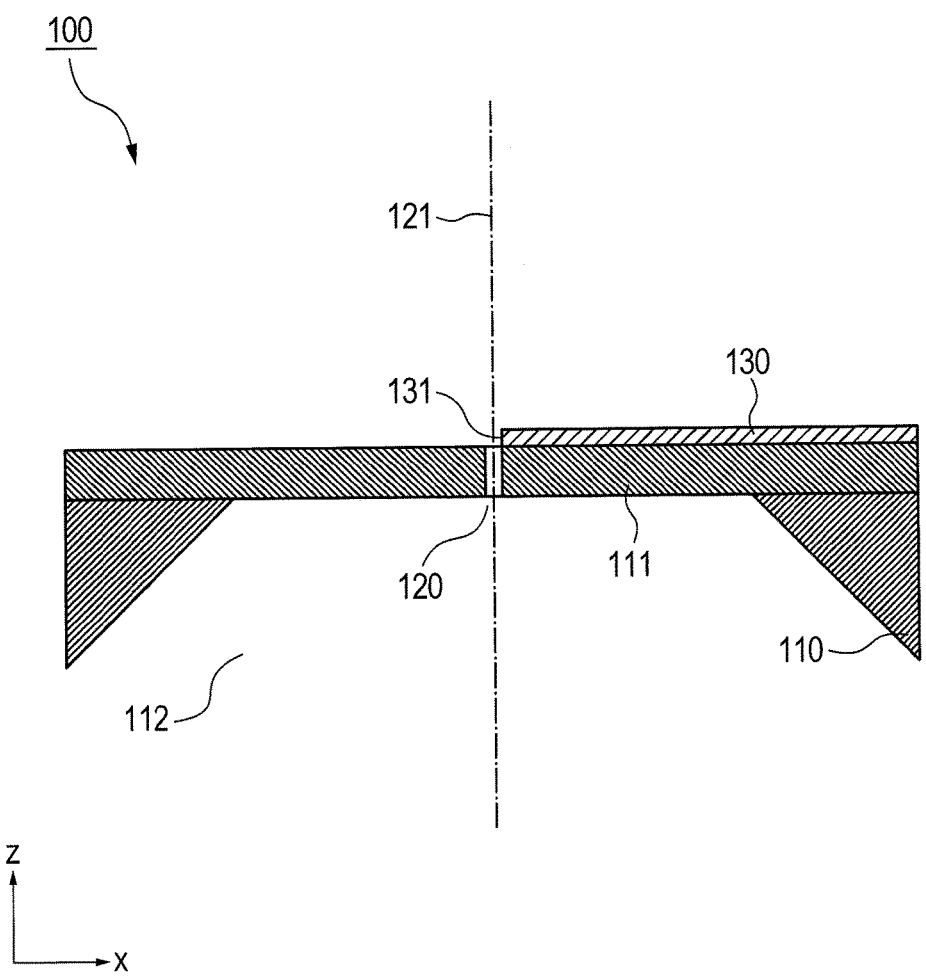
FIG. 2 is an enlarged schematic diagram of the cross section of the nanopore chip.

FIG. 2 is an enlarged schematic diagram of a xz cross section containing the central axis of the nanopore 120 in the nanopore chip 100 according to this embodiment. The substrate 110 has a thin film part 111 at the substrate surface, namely in the upper part along the z axis, and additionally, an electroconductive thin film 130 above the thin film 111 along the z axis. The substrate has a tapered dent (hereinafter, simply referred to as a "window 112") in the lower part along the z axis, where the thin film part 111 of the substrate is exposed. The nanopore 120 is formed in the thin film part 111 of the window 112. As shown in the figure, one edge 131 of the electroconductive thin film 130 faces the top of the opening of the nanopore 120. As approximately shown in FIG. 1, the edge 131 is formed into a sharp tip in a plan view, which faces the nanopore 120.

Figure 3:
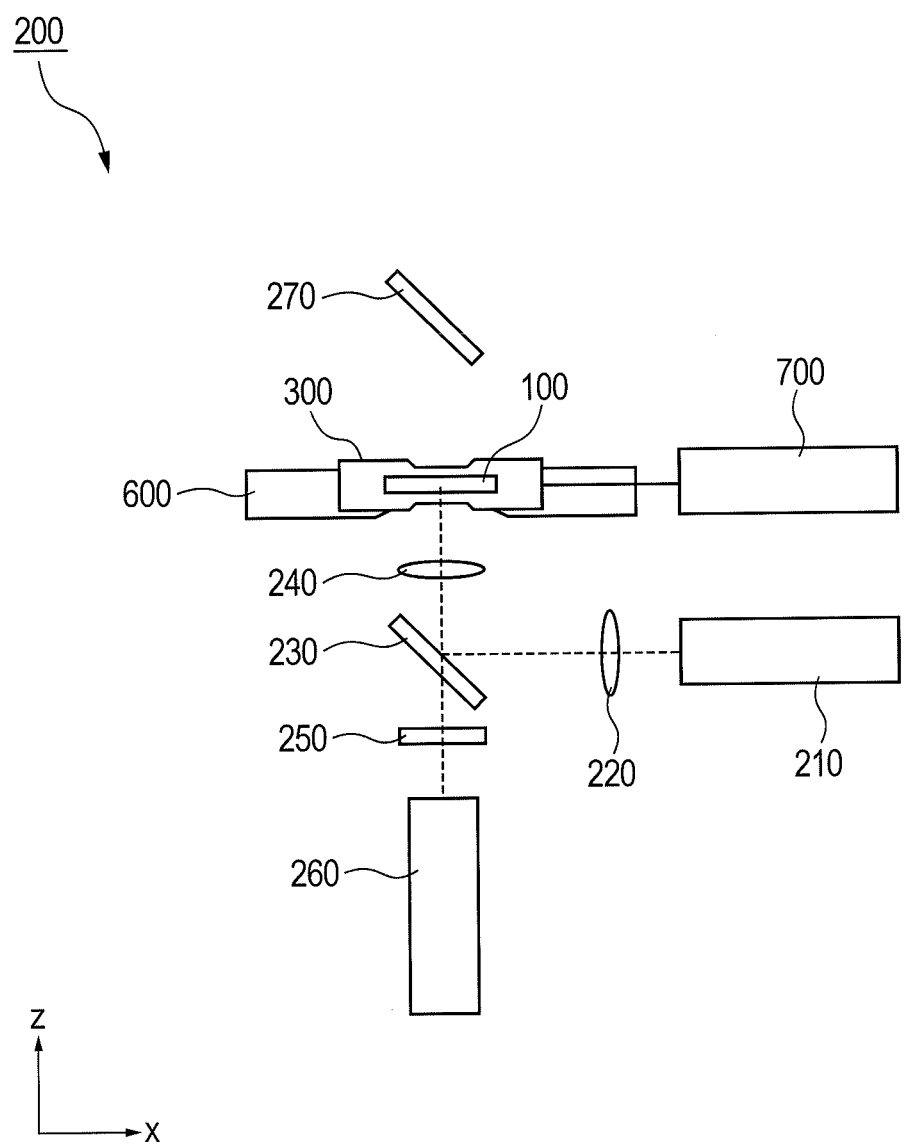
FIG. 3 is a schematic diagram of the construction of a biopolymer property analysis device.

Next, an example of the construction of a biopolymer property analysis device of the present invention will be described referring to FIG. 3. FIG. 3 is a schematic diagram of the construction of the biopolymer property analysis device 200 according to this embodiment. The analysis device 200 is composed of a light source 210, a lens 220, a half mirror 230, an objective lens 240, a filter 250, a spectroscopic detector 260, a terminator 270, a high precision xyz stage 600, an instrument for driving the sample 700, a sample cell 300, a measurement control device (not indicated in the figure), for example, a personal computer, or the like. The sample cell 300 contains the nanopore chip 100.

Figure 4:
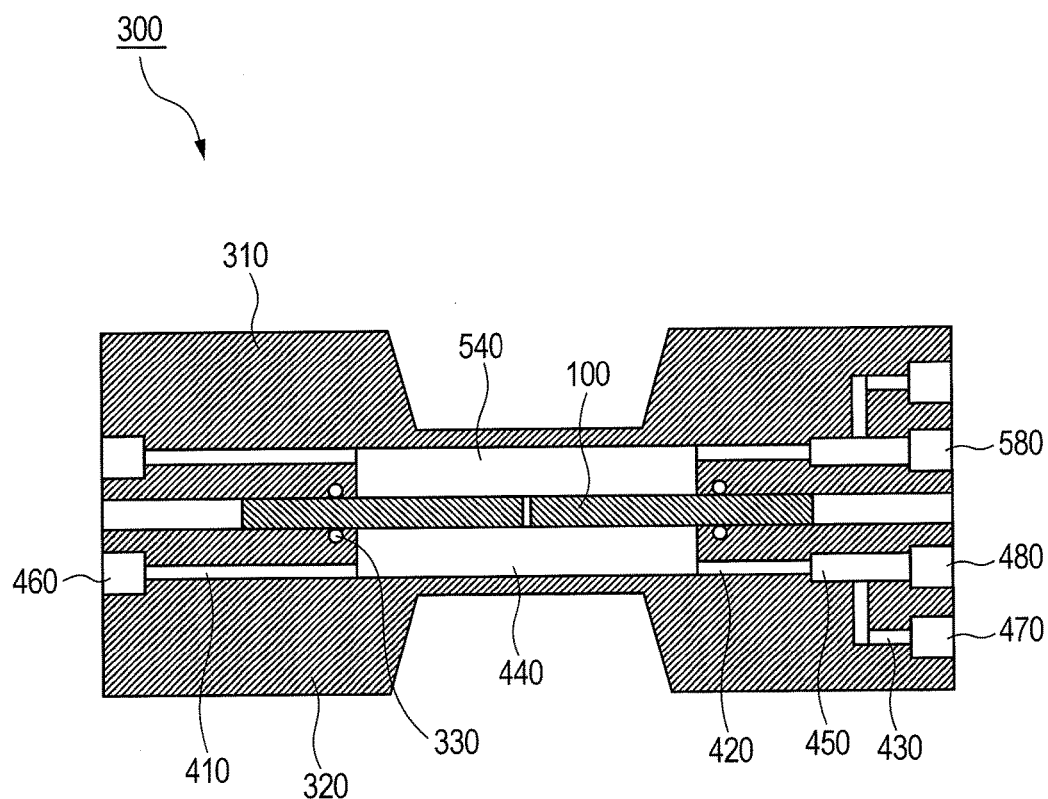
FIG. 4 is a sectional view of the outline of the construction of a sample cell.

FIG. 4 is a view of a xz cross section showing the outline of the construction of the sample cell 300. The sample cell 300 is composed of a nanopore chip 100, an upper member 310, a lower member 320, screws (not shown in the figure), and the like. Inside of the lower member 320, an O-RING 330, a sample flow channels 410, 420, and 430, a sample chamber 440, and an electrode chamber 450 are formed, and also a sample connection ports 460, 470, and an electrode connection port 480 are formed. A tubing for sending the sample solution (not indicated in the figure) is air-tightly coupled to the lower member 320 via the sample connection ports 460, 470, and an AG/AgCl electrode (not indicated in the figure) is further air-tightly connected thereto via the electrode connection port 480. The AgCl end of the Ag/AgCl electrode (not indicated in the figure) is contained in the electrode chamber 450, and the end (hereinafter, simply referred to as a silver end) containing Ag thereof is exposed to the outside of the electrode connection port 480. The tubing for sending the sample solution, sample connection port 460, sample flow channel 410, sample chamber 440, sample flow channel 420, electrode chamber 450, sample flow channel 430, sample connection port 470, tubing for sending the sample solution are air-tightly (and free of air bubbles) filled with a sample solution (not indicated in the figure). Accordingly, the sample solution in the sample chamber 440 comes into contact with the Ag/AgCl electrodes in the electrode chamber 450, and both the sample solution and the Ag/AgCl electrodes are electrochemically conducted. The aforementioned descriptions of the lower member 320 are applicable to the upper member 310.

Next, the outline of the operational principle of the nanopore chip of the present invention will be described referring to FIG. 1 to FIG. 8. First of all, preparation for the sample cell 300 is performed. Specifically, the nanopore chip 100 is inserted between the upper member 310 and the lower member 320, and pressurized with the O-RING 330 to air-tightly attach the upper and lower sample chambers 540 and 440. As a sample solution, 100 mM KCl aqueous solution is introduced from the tubing for sending the sample solution, and the sample chambers 540, 440, and the electrode chamber 450 are filled with the sample solution.

Next, the sample cell 300 is installed in the analysis device 200. Specifically, the sample cell 300 is fixed to the high precision stage 600. An optical system is caused to focus on the thin film part 111 of the nanopore chip 100 in the sample cell 300 using the high precision stage 600 and optics for visual examination (not indicated in the figure). Two Ag/AgCl electrodes installed in the sample cell 300 are coupled to the instrument for driving the sample 700. The instrument for driving the sample 700 houses a voltage source or current source so as to be capable of applying voltage in the lower sample chamber 440 in reference to that of the upper sample chamber 540.

The optical system of the analysis device operates as descried below. Specifically, a laser beam emitted from the light source 210 is shaped through the lens 220, and then reflected against the half mirror 230 and condensed in the thin film part 111 of the nanopore chip 100 with an objective lens 240. The laser beam passing through the thin film part 111 irradiates the electroconductive thin film 130 and a strong near field is generated at the edge 131 (facing the opening of the nanopore 120) of the electroconductive thin film 130. When a chemical substance (biopolymer) is introduced in the region (hereinafter, simply referred to as a near field) where the near field has been formed, the near field light excites the chemical substance, causing the chemical substance to generate a Raman scattered light specific thereto. The Raman scattered light is condensed with the objective lens 240 and caused to pass through the half mirror 230. A Rayleigh scattered light and anti-Stokes line are removed using the filter 250; the Stokes line of the Raman scattered light is caused to enter the spectroscopic detector 260; and the Raman scattering spectrum (Stokes line) is spectroscopically analyzed using the spectroscopic detector 260 and detected. The light passing through the thin film part 111 and the electroconductive thin film 130 is absorbed at the terminator 270 or diffuses in the unrelated direction. The main optical path is shown by means of a broken line in FIG. 3.

The procedure for measuring DNA, as an example, of the biopolymer to be measured will be described below. In brief, for example, 10 kb (knt)-length single stranded DNA dissolved in 100 mM KCl aqueous solution is used to prepare sample solution of 1 nM concentration. This sample solution is introduced in the sample chamber 440 as the lower sample solution. When 100 mV negative voltage is applied in the lower sample chamber 440 using the instrument for driving the sample 700, ions in the sample solution pass through the nanopore 120 by means of electrophoresis and current (ionic current) flows. Since only water and KCl exist initially in the near field, only the Raman scattering spectrum of water is observed. DNA passes up to the upper sample chamber 540 from the lower sample chamber 440 through the nanopore 120 by means of electrophoresis. When DNA passes through the nanopore 120, a nucleic acid base, which is a unit element of DNA, penetrates into the near field formed at the edge 131 of the electroconductive thin film 130. Then, a Raman scattered light specific to the base is generated and the Raman scattering spectrum is obtained by the spectroscopic detector 260. During electrophoresis of DNA, the nucleic acid base also moves into and migrates out from the near field. Then, the Raman scattered light specific to the base extinguishes. When electrophoresis is further continued, the step of causing the next base on the DNA sequence to penetrate into and migrate out from the near field is sequentially repeated in the same manner, and the Raman scattering spectrum corresponding to the base sequence of DNA is obtained over time. The intensity of the scattered light at the characteristic wavenumber of each of bases (hereinafter, simply referred to as specific band) is obtained over time, and its change over time is converted to spectral information for each base using the difference method described in Non-Patent Document 3, or the like, and the spectral information is analyzed to determine the DNA base sequence. The operational principle of this embodiment has been described so far.

Hereinafter, the individual components will be described below in detail.

The nanopore chip 100 according to this embodiment was fabricated by following the procedure described below. A silicon wafer was used as a substrate 110 and an about 20 nm thickness oxide layer was formed on the surface thereof by LPCVD (low pressure chemical vapor deposition) (the oxide layer finally serves as the thin film part 111). A window pattern was formed at the bottom of the substrate by electron beam (EB) lithography; the surface layer was removed by reactive ion etching; and the silicon was removed by KOH (potassium hydroxide) wet etching to form the window 112 having the thin film part 111. A silver thin film was formed on the surface of the substrate as an electroconductive thin film 130 by sputtering. The thickness of the silver thin film was about 5 nm. Resist was applied on the silver thin film; a triangle pattern was formed by electron beam lithography as shown in FIG. 1; silver in the region excluding the triangle pattern was removed by etching; and then the resist was removed. Finally, the substrate was observed under a transmission electron microscope (TEM), and an electron beam was irradiated on the triangle edge 131 from the TEM to form the nanopore 120. The internal diameter of the nanopore was about 10 nm. In this embodiment, the thin film part 111 was made of, but not limited to, silicon oxide but silicon nitride or the like can be used in the same manner.

The electroconductive thin film 130 according to this embodiment can be optically defined as a light scattering substance. In this embodiment, silver was used as the material for the electroconductive thin film 130, but the material is not limited to silver and any of general materials having conductivity or light scattering property may be used. Generally, metals can be suitably used. Other metals allowed for the electroconductive thin film include the metals including the platinum group, such as platinum, palladium, rhodium, and ruthenium; gold; and copper.

The shape of the electroconductive thin film 130 according to this embodiment was triangle and 30 degrees was used for the angle of the vertex of its edge 131 and 100 nm, which was sufficiently shorter than the wavelength of excitation light (531 nm) described later, was used for the length of the triangle in the x direction. The shape of the electroconductive thin film (scattering substance) preferable for forming near field light is described in detail in Japanese Unexamined Patent Application Publication No. 2009-150899 (hereinafter, simply referred to as a "fourth example, according to prior art") and the shape of electroconductive thin film 130 of the present invention can be also selected by following the forth example according to prior art. Giving an example, as described in the fourth example according to prior art, with a smaller angle (acute angle) of the vertex of the edge 131, charges easily concentrate on the edge, achieving a high intensifying effect on the near field. It should be noted that in the present invention, since other edges than the edge 131 of the electroconductive thin film (hereinafter, simply referred to as other edges) can be disposed so as to be masked by the substrate 110, the near field light formed at other edges can be minimized. Accordingly, the optimal value for the angle of the vertex can be extended to lower values compared with that of the fourth example according to prior art. However, if the angle is too small, the area of the electroconductive thin film is reduced and the efficiency in using incident light energy is also reduced. Accordingly, 10 to 80 degrees, preferably 20 to 60 degrees can be preferably used for the angle of the vertex.

As described in the fourth example according to prior art, the vertex of the triangle edge 131 may not be always shaped into a strict point, and a round shape with curvature of radius smaller than or equal to a certain level, preferably smaller than or equal to 10 nm may be used. Angles other than the triangle edge 131 are preferably more obtuse than that of edge 131. Moreover, the shape of the electroconductive thin film 130 is not limited to a triangle, and any shape having the edge 131, the angle of which vertex is acute-angled as aforementioned may be used, while any of shapes such as a round-shape with no angle, and a shape with an angle more obtuse than that of the vertex of the edge 131 can be arbitrarily selected for the shapes of other edges. In other words, any of various kinds of shapes including a sector; a mixture of round shape and triangle; and polygons such as a triangle, tetragon, and pentagon can be selected for the shape of the electroconductive thin film 130. In this embodiment, since the near field light formed in the region masked by the substrate 110 does not affect the measurement, the shape of the electroconductive thin film can be arbitrarily selected in the masked region.

In this embodiment, transparent members were used for the sample cell 300, in particular, for the central portions of the upper member 310 and the lower member 320 (where the sample chambers 440, 540 are separated from the outside). Acceptable transparent members include glass, quartz, and plastic materials such as acrylic resin with high transparency at the wavelength of the light source. The use of the transparent member in the central portion of the lower member 320 allows the laser beam emitted from the light source 210 to be efficiently irradiated on the nanopore chip 100. Moreover, the use of the transparent member in the central portion of the upper member 310 allows the transmitted light and the scattered light to pass through the nanopore chip 100 without reflection, suppressing the background light. In this context, for simplification, FIG. 3 illustrates such a process that the laser beam emitted from the light source 210 is reflected against the half mirror 230 and then enters the nanopore chip 100 in the almost perpendicular direction shown in the figure, but actually, the incident angle of the laser beam is preferably inclined away from the normal line of the nanopore chip 100. Furthermore, in FIG. 3, for simplification, none is disposed between the objective lens 240 and the nanopore chip 100, but an appropriately-shaped slit is preferably formed between the objective lens 240 and the nanopore chip 100. The use of these constructions avoids such malfunction that the light reflected against the thin film part 111 of the nanopore enters the spectroscopic detector 260, so that background light is suppressed, and a high S/N ratio is achieved.

In FIGS. 3 and 4, the objective lens 240 is slightly separated from the sample cell 300 (nanopore chip 100 contained therein) but actually, they are preferably disposed closely to each other as much as possible. The objective lens 240 and the nanopore chip 100 is placed close to each other within a distance less than or equal to 3 mm, preferably less than or equal to 1 nm. This enables efficiency of excitation from an excitation light and efficiency of condensation from a scattered light to be increased, achieving high-sensitivity measurement. Moreover, an immersion-liquid type objective lens 240 is preferably used. The objective lens with high aperture is preferably used, more preferably those with number of apertures ≥0.8 is used.

The biopolymer property analysis device according to this embodiment was built up based on a microscope-integrated laser Raman spectroscope similar to the third example according to prior art. It should be noted that the stage supplied with the microscope was used for the xyz high precision stage 600 and a piezostage for AFM was not used. In this embodiment, a Kr ion laser with output of 1 mW and wavelength of 531 nm was used for the light source 210. A laser and its wavelength can be arbitrarily selected. A function generator was used for the instrument for driving the sample 700 and the function generator was used in combination with an attenuator (resistance type potential divider). The instrument for driving the sample 700 is capable of outputting DC at an output voltage ranging 0 to ±10V or any waveform. The any waveform is exemplified by a pulse wave characterized in that it can be arbitrarily output with the peak pulse time duration of the order of 10 ns and the peak voltage of the pulse within the same voltage range as aforementioned.

Hereinafter, the operational principle of this embodiment will be described in detail.

The substrate 110 of the nanopore chip 100 is made mainly of silicon (Si). The thickness of the substrate is about 700 µm. The thin film part 111 of the substrate is made of silicon oxide ($SiO_2$) and the thickness thereof is thin, about 20 nm. Accordingly, a laser beam passes through the thin film part 111 in the window 112 of the substrate and irradiates the electroconductive thin film 130. Irradiation on the electroconductive thin film 130 with the laser beam causes a strong near field to occur at the edge 131 thereof. The laser beam polarized in the direction toward the tip of the edge, namely in the x axis direction, is preferably used. The thickness of the near field in the z direction is almost identical to that of electroconductive thin film 130, namely about 5 to 10 nm.

The thickness of the substrates 110 is about 700 µm in the region excluding the window 112. Since Si, which is the material for the substrate 110, absorbs, reflects, and scatters the laser beam, almost no laser beam reaches the thin film part formed in the region excluding the window 112 and the electroconductive thin film 130 formed thereon. For this reason, the formation of the near field is suppressed on the electroconductive thin film 130 in the region excluding the window 112. In other words, the aforementioned construction is characterized in that it allows the formation of the near field on the electroconductive thin film 130 to be limited mainly to the window 112, in particular the target edge 131, suppressing the background light in the region excluding the target edge. Moreover, preferably, anti-reflective coating is applied on the surface of the substrate 110 in the region excluding the window 112; specifically, for example, the surface is roughened or an absorptive material is applied on the surface. This construction has such effects that the reflection of the laser beam in the region excluding the target window 112 is suppressed and the background light is also suppressed.

In connection with the constructions used this embodiment and a variation thereof described later, the formation of the near field was analyzed by means of simulation and compared to each other. Hereinafter, the result will be described below.

As with this embodiment, the distribution of the near field light generated in the vicinity of a triangle conductor, when light is caused to enter therein, was calculated by the FTDT method (time domain optical progression solver OptiFDTD, Optiwave System Inc.). In this calculation process, the dimensions of the region to be analyzed were 0.3×0.2×2.6 um in the X, Y, and X directions, respectively (note that the X, Y, and Z coordinate system is used exclusively in FIGS. 5 and 6, the direction of Y is perpendicular to a XZ plane). The conductor made of silver had thickness of 10 nm and the acute angle of the tip was 90 degrees. A plane wave with wavelength of 780 nm was used for an incident wave and a wave source was generated at the point one-wavelength apart from the surface of the conductor ($\lambda$=780 nm). The incident wave was polarized in the x direction. For boundary conditions, a cyclic boundary condition on the xy side and an absorptive boundary condition on the z side were used. The uniform mesh size of 2.6 nm was used in the entire region to be calculated.

FIG. 5A is a schematic diagram of the analyzed construction. In FIG. 5B, the calculated result of the XY-plane distribution of the ratio between the intensity-density of the near field (I) and the intensity-density of the incident wave (In) was plotted along the vertical axis. As shown in the figure, the most intense light field occurred at the tip of the thin film triangle and its maximum value was about 1100-fold in terms of incident intensity ratio.

In addition, calculation was performed for another case where two triangle thin films were disposed such that their vertexes faced 3 nm apart from each other, and the result was shown in FIGS. 6A and 6B. These constructions correspond to those according to a variation described later. In this case, about 7100-fold effectiveness of intensification was achieved.

Putting together the results of simulation described above suggested that the use of the electroconductive thin films, which have the constructions and shapes used in this embodiment and in particular, the variation described later, causes the near field having strong effect of intensifying the light-induced electric field to be formed.

At the point when a Raman scattered light derived from the base is observed immediately after DNA has penetrated into the nanopore 120, the absolute value for a voltage to be applied to the lower sample chamber 440 can be decreased using the instrument for driving the sample 700 to reduce the speed of DNA electrophoresis. When the polarity of voltage is reversed with the absolute value for applied voltage decreased (positive voltage is applied to the lower sample chamber 440), the electrophoresis of the DNA chain can be caused at a lower speed and in the reverse direction. By continuing the electrophoresis of the DNA chain under this condition until no Raman scattered light derived from the base can be observed, the tip of the DNA chain can be retracted to the outside of the near field. From this state, by restoring the polarity of voltage to its original state with the absolute value for applied voltage decreased (negative voltage is applied to the lower sample chamber 440), the electrophoresis of the DNA chain can be caused to be performed slowly from the head thereof, allowing the measurement of the Raman scattered light to be repeated. This enables the base to be measured to be retained inside the near field over the time duration required for measuring the Raman scattering spectrum.

It is possible that a constant voltage (DC) is applied to the lower sample chamber 440 using the instrument for driving the sample 700. Alternatively, the applied voltage can be in the form of a pulse wave to repeat the start and stop of DNA electrophoresis at short intervals. In this case, the pulse width of the pulse wave can be adjusted (pulse width modulation). When the ratio of the time duration (duty ratio), during which the pulse is ON in one cycle, is decreased and the ratio of OFF is increased, the electrophoresis time can be shortened in one cycle while the stopping time can be lengthened. Giving an example, since the use of a function generator with frequency band of 100 MHz allows the plush width to be varied in the unit of 10 ns, the duty ratio can be adjusted at the resolution of 1/1,000,000 assuming that the length of one cycle is, for example, 10 ms. In other words, the average moving speed of the DNA chain can be adjusted (to the lower level) at a very high resolution by means of the duty ratio. Moreover, when the duty ratio is adjusted together with the height of the pulse wave (pulse height modulation), the speed of electrophoresis can be adjusted more precisely. Control of electrophoresis voltage and the pulse width thereof allows the target base to be retained in the near field over the time required for measuring the Raman scattering spectrum with sufficient precision. Furthermore, when the Raman scattering spectrum is obtained within the stopping time, such a problem is eliminated that a variation in signal occurs due to the target to be measured enters or migrates from the near field, so that measurement values can be obtained with higher precision.

The polarity of the voltage to be applied to the lower sample chamber 440 can be cyclically switched between positive and negative. In this case, adjusting time-averaged voltage so as to be slightly negative, as compared with a more simple method of applying only a constant negative voltage, allows the DNA chain to be elongated stably and penetrate through the nanopore 120 slowly up to the upper sample chamber 540 by means of electrophoresis, achieving the measurement of the Raman scattered light for each of bases in the DNA chain with high sensitivity.

Another effective method for controlling the electrophoresis speed of the DNA chain is to increase the viscosity of the sample solution. By adding a mechanism for controlling the temperature in the vicinity of the nanopore chip to decrease the temperature of the sample solution, the viscosity of the sample solution is increased and the Brownian motion of the DNA chain is suppressed, providing conditions suitable for measuring the DNA Raman scattered light. The addition of a polymer other than the polymer to be measured in the sample solution can increase the viscosity of the sample solution and the conformation of the DNA chain can be formed into a linear shape, also providing a condition suitable for measuring the Raman scattered light of the DNA chain. A separation medium for capillary electrophoresis may be used as the additional polymer. The use of preferably a polymer having a size larger than the nanopore, more preferably a three-dimensionally crosslinked polymer can increase only the viscosity without interruption of measurement. Referencing to FIG. 13 described later, in particular, the intensified field, namely the region to be measured can be contained inside the nanopore and in this case, only the biopolymer to be measured, for example, only the DNA chain can be caused to penetrate into the measurement region with no polymer other than that to be measured penetrating into the measurement region, eliminating the Raman scattered light generated by a polymer not to be measured.

To reduce the DNA electrophoresis speed, any of other methods for implementing and correctly controlling a minor electrophoresis speed can be used. A first method allows a pair of measurement electrodes capable of detecting the voltage applied between the upper and lower sample chambers (440 and 540) at high sensitivity to be newly (in addition to previously disposed Ag/AgCl electrodes) disposed in each of the upper and lower sample chambers. In this case, feedback control of the voltage to be applied to the Ag/AgCl electrodes based on the voltage measured actually using the pair of measurement electrodes allows a specific minute voltage to be applied correctly between the upper and lower sample chambers. As a second method, a potentiostat technique can be used. In this case, considering the pair of previously disposed Ag/AgCl electrodes to be a sample electrode and its counter electrode, respectively, a reference electrode can be newly disposed in each of the sample chambers 440, 540 on the counter electrode side to control current flowing through the sample electrode and the counter electrode such that the voltage, for which value has been previously set, is applied between the sample electrode and its counter electrode. The aforementioned method allows the specific minute voltage to be applied correctly between the upper and lower sample chambers 440 and 450 to implement and control correctly the minute electrophoresis speed. As a third method, a galvanostat technique can be used. In this case, considering a pair of previously disposed Ag/AgCl electrodes to be the sample electrode and its counter electrode, respectively, feedback control of current can be performed such that the current, for which value has been previously set, flows, while the current from one electrode to another electrode is being controlled. This technique allows the given minute current to flow correctly between the upper and lower sample chamber 440 and 450 to implement and control properly the minute electrophoresis speed. As a fifth technique, a method for giving conductivity to the nanopore substrate by fabricating the nanopore substrate using an impurity-doped semiconductor to control the potential on the surface of the nanopore substrate can be used. The use of a potentiostat, or the like allows the potential on the surface of the nanopore substrate to be controlled based on the potential in the solution; for example, the application of a positive voltage to the substrate enables the negatively-charged sample DNA to be adsorbed on the substrate and its moving speed to be suppressed. Control of the voltage on the substrate so as to be shaped into a pulse can implement step-feeding of sample. Moreover, contrary to the aforementioned step, the application of a negative voltage on the substrate can suppress non-specific absorptions of DNA onto substrates for easy sample replacement.

Other techniques for controlling the speed, at which the DNA chain passes through the nanopore 120, will be described below. To exert a force on the DNA chain for causing it to pass through the nanopore by means of electrophoresis and an opposite force, applying differential pressure between the sample solutions filled in the upper and lower sample chambers 440 and 450 can reduce the speed at which the DNA chain passes through the nanopore. Giving an example, applying atmospheric pressure to the sample solution, which is filled in the lower sample chamber 440, and a pressure higher than or equal to atmospheric pressure to the sample solution, which is filled in the upper sample chamber 540, by means of a pump mechanism or piezoelectric mechanism, allows the pressure to be applied in the direction toward the lower sample chamber 440 from the upper sample chamber 540, namely in the direction opposite to that of electrophoresis of the DNA chain. This differential pressure may be controlled by means of a difference in composition between the upper and lower sample chambers, for example, an osmotic pressure based on a difference in ion concentration, or the like. The sample solution may be moved through the nanopore 120 in the form of a bulk in the direction opposite to that of electrophoresis of the DNA chain, namely in the direction toward the lower sample chamber 440 from the upper sample chamber 540, by means of this differential pressure, to reduce the speed at which the DNA chain passes through the nanopore. This type of sample solution movement can be implemented by electrically charging the internal surface of the nanopore 120 to cause electroosmotic flow inside the nanopore 120. Sample solution movement is capable of bringing further effects described below. In this case, the sample solution can move such that it envelopes the DNA chain to cause it to be locally contained in the vicinity of the central axis of the nanopore 120 while the DNA chain is being elongated along the central axis. This technique allows each of bases on the DNA chain to pass through the center of the intensified field stably, achieving high precision measurement of the Raman scattered light.

Figure 7:
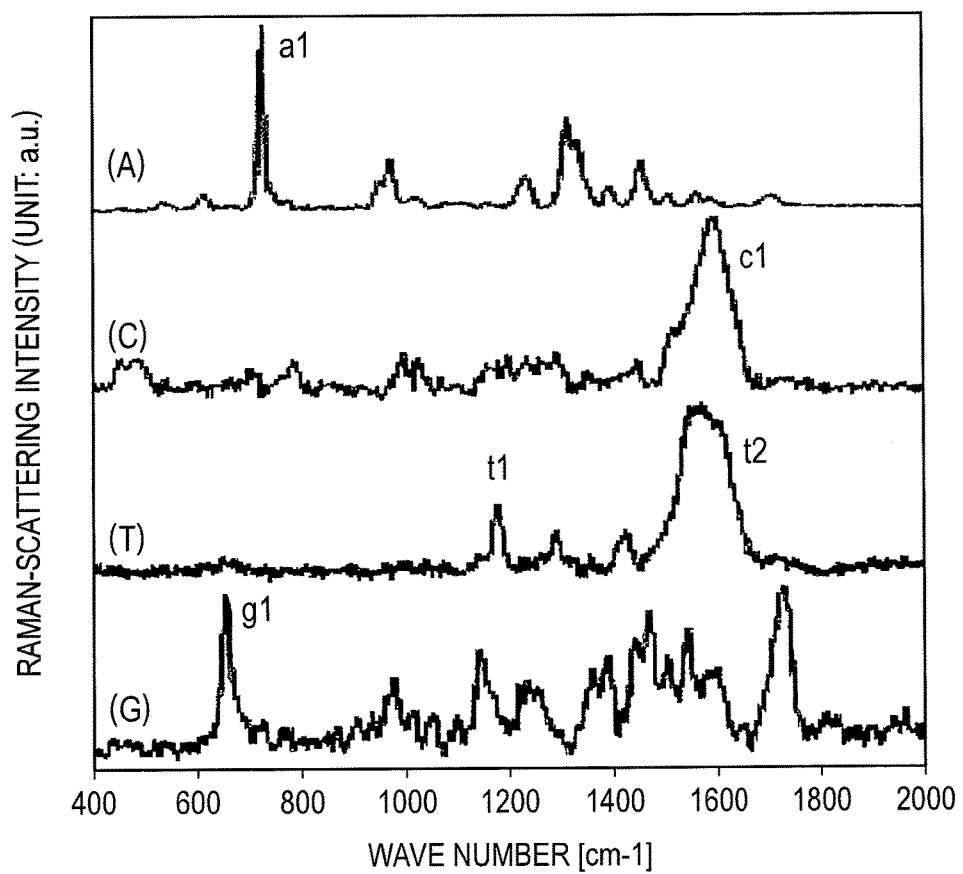
FIG. 7 shows the typical Raman scattering spectra of nucleic acid bases.

FIG. 7 shows a typical example of the intensities (spectra) for the Raman scattered lights generated by nucleic acid bases. Each of four types of bases A, C, T, and G shows the peak intensity of their scattered light at their characteristic wavelength (hereinafter, also simply referred to as a "specific band"). The peak specific bands for A, T, and G are represented by a1, t1, and g1, respectively and their wave numbers are about 730, 1180, and 650 cm$^{-1}$, respectively. The position of the peak of C, c1 (namely, about 1730 cm$^{-1}$) is overlapped by the position of the peak of T, t2 (namely, 1600 cm$^{-1}$) but T and C can be discriminated from each other considering whether the specific band d1 specific to T appears or not. In other manners than that aforementioned, the specific bands for C and T, C:1260 cm$^{-1}$ and T:1360 cm$^{-1}$ may be applicable.

Figure 8:
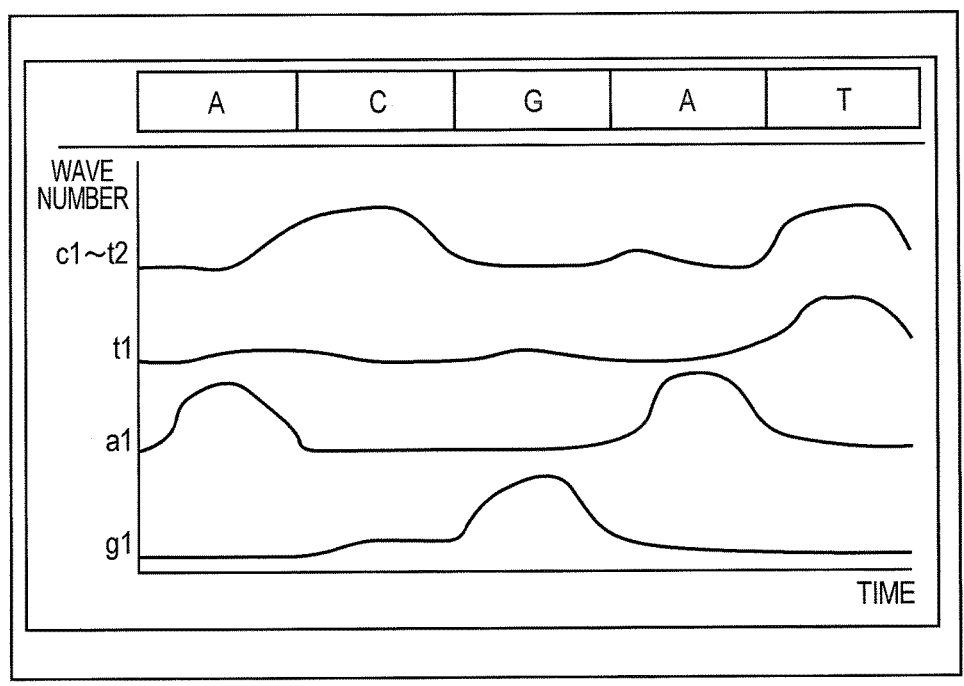
FIG. 8 is an image displayed on an output screen, which corresponds to a procedure for determining a base sequence based on the spectral information for each base.

Referencing to FIG. 8, the procedure for determining base sequences based on spectral information for each base obtained by the difference method will be described below. FIG. 8 shows an image corresponding to this procedure displayed on a PC output screen. The spectral information represented by specific bands a1, t1, g1, c1, and t2 for each base obtained by the difference method is displayed in the lower part of the screen in terms of horizontal axis vs. time and vertical axis vs. signal intensity (wavenumber). Since the specific bands c1 and t2 are partially overlapped by each other as aforementioned, the information for them is displayed in the wavenumber range from c1 to t2. The bases are determined to be A, C, G, or A in reference to their peak specific bands appearing with time, namely a1, c1 to t2 (without t1), g1, a1, c1 to t2 (with t1) in the example shown in FIG. 8. The determined sequence is displayed in the upper part of the screen, stored in the PC, and output to the outside as the result.

In this embodiment, the technique for analyzing DNA by obtaining the spectral information for A, C, T, and G has been exemplified but the application of the present invention is not limited to this embodiment. Giving an example, analyzing the spectrum of U allows RNA analysis. Moreover, obtaining the spectrum of methylated cytosine enables information for DNA methylation to be directly readout. Furthermore, obtaining the spectrum of amino acid enables peptide and protein to be analyzed and obtaining the spectrum of sugar enables a sugar chain to be analyzed.

The biopolymer property analysis chip using a solid state nanopore according to this embodiment is characterized by high contractual stability and high reliability. Moreover, the biopolymer property analysis device according to this embodiment determines the type of a monomer using the Raman spectra as an indicator. The spectrum, which has two-dimensional information, namely a wavenumber vs. intensity pattern, is characterized in that it provides an exponentially large volume of information compared with one-dimensional information for the intensity of tunneling current, and has high ability to identify in quantitative analysis; namely, it has high ability to identify bases. In this embodiment, the near field was fixed to the opening of the nanopore 120 and the instrument for driving the sample 700 was used to cause to move DNA by means of electrophoresis and control the relative position between the DNA and the near field. This eliminates the needs for immobilizing nucleic acid to the solid state substrate 110 in advance, and for a high precision stage, and AFM. Moreover, the need for careful operation for causing the AFM probe to two-dimensionally scan at the accuracy of sub-nm is eliminated. In other word, the biopolymer property analysis chip is characterized by simple device construction and operation.

Variation of the First Embodiment

Figure 9:
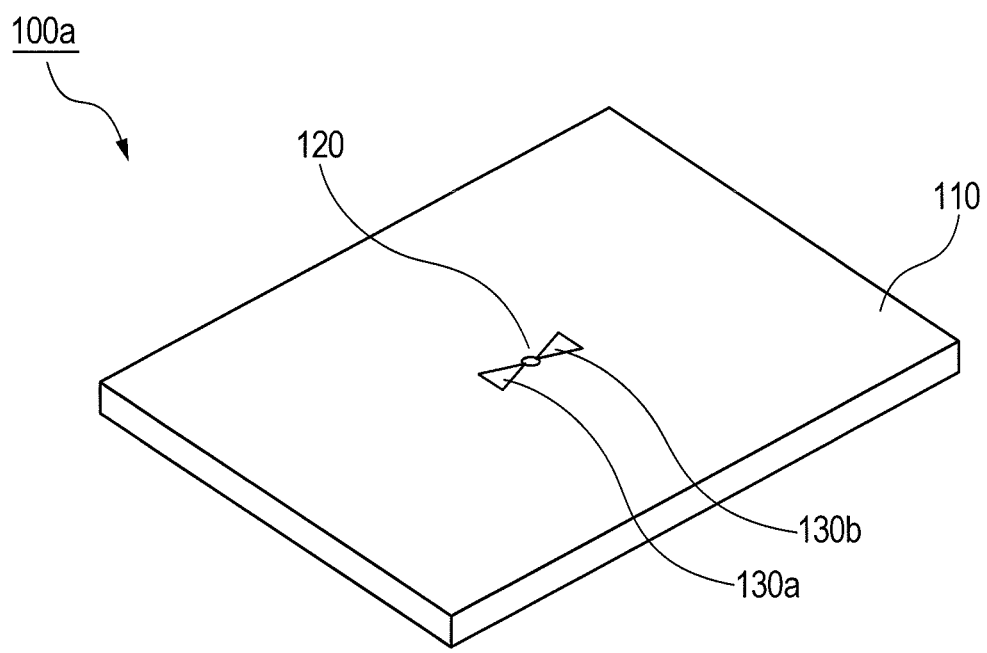
FIG. 9 is a schematic diagram of a variation of the nanopore chip for analyzing the characteristics of the biopolymer.
Figure 10:
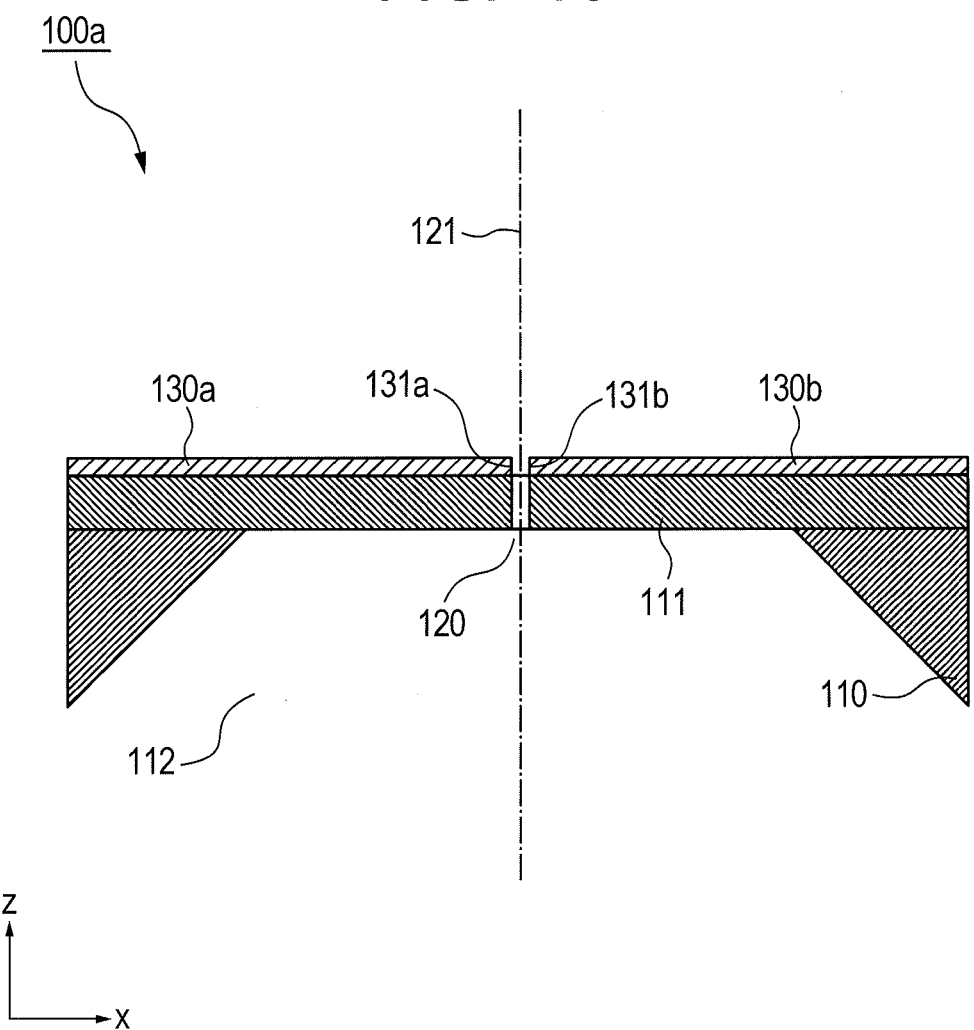
FIG. 10 is an enlarged schematic diagram of the cross section of the variation of the nanopore chip.

According to a variation of the first embodiment, a nanopore chip 100a structured as described below can be implemented. FIG. 9 is a schematic diagram of the nanopore chip 100a according to this variation. As shown in the figure, the nanopore chip 100a is composed of the substrate 110, the nanopore 120, the electroconductive thin films 130a, 130b, or the like. Specifically, the variation is different from the first embodiment in that it has two electroconductive thin films corresponding to the electroconductive thin film 130 in the first embodiment, and one of them (electroconductive thin films 130a, 130b) is turned by 180 degrees so as to be displaced with the edge thereof facing the nanopore. FIG. 10 is an enlarged schematic diagram of the xz cross section containing the central axis 121 of the nanopore 120 in the nanopore chip 100a according to this variation. As shown in the figure, the electroconductive thin films 130a, 130b are formed on the thin film 111 along the z axis, and their edges 131a, 131b face the top of the opening of the nanopore 120, being opposed to each other. In brief, the electroconductive thin films 130a and 130b are disposed almost the same distance as the diameter of the nanopore 120 apart from each other.

The analysis device for the nanopore chip 100a according to this variation and the operation thereof are similar to those according to the first embodiment. As with the first embodiment, the laser beam polarized in the direction where two edges are coupled, namely along the x axis is preferable used. The variation is different from the first embodiment in that the near field light is generated in the void formed between the edges 131a, 131b of the electroconductive thin films 130a, 130 by means of irradiation with a laser beam. As suggested from the result of simulation (FIG. 6) shown in the first embodiment, the near field lights derived from these two electroconductive thin films are intensified by each other, resulting in the intensified intensity of the near field. Moreover, the disposition of the electroconductive thin films 130a, 130b limits the distribution of the near field in the x direction, localizing it to the extent of almost the diameter of the nanopore 120. As a result, the near field according to this variation has high symmetry of shape, namely high uniformity. Furthermore, this variation is characterized in that since the intensity of the near field is high, about 7,000-fold in terms of the ratio of incident light amount as aforementioned (FIG. 6), it provides high sensitivity; the near field is spatially uniform; and spatial resolution is high.

As another application of this variation, the construction, in which three or more electroconductive thin films are used, can be used. Giving an example, the edges of four electroconductive thin films are disposed so as to face the nanopore in the form of a cross. It is characterized in that since the electroconductive thin films are disposed so as to have 90 degrees of rotating symmetry around the central axis, an intense near field can be induced at any of the edges of the pair of electroconductive thin films faced to each other, simply by causing the laser beam to enter in the direction toward the central axis without the need for controlling the orientation of laser polarization in the xy direction.

Second Embodiment

Multinanopore Analysis Device Construction

Figure 11:
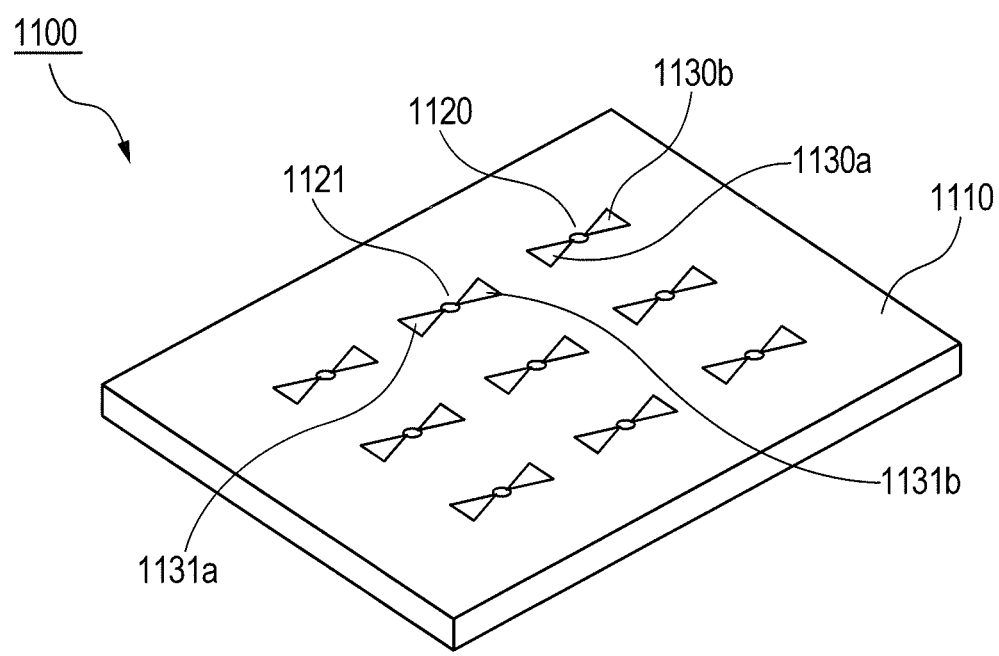
FIG. 11 is a schematic diagram of a multinanopore chip according to a second embodiment.

One example of the construction of a multinanopore chip for biopolymer property analysis according to the second embodiment of the present invention will be described referring to FIG. 11. FIG. 11 is a schematic diagram of the multinanopore chip 1100 for biopolymer property analysis according to the second embodiment. As shown in the figure, the nanopore chip 1100 is composed of a substrate 1110, nanopores 1120, 1121, and electroconductive thin films 1130a, 1130b, 1131a, and 1131b, or the like. As shown in the figure, the multinanopore chip 1100 according to this embodiment has a plurality of unit structures composed of nanopores and electroconductive thin films facing to each other, or the like, according to the aforementioned variation, namely the unit structures shown in FIG. 10, on a single substrate 1110.

Figure 12:
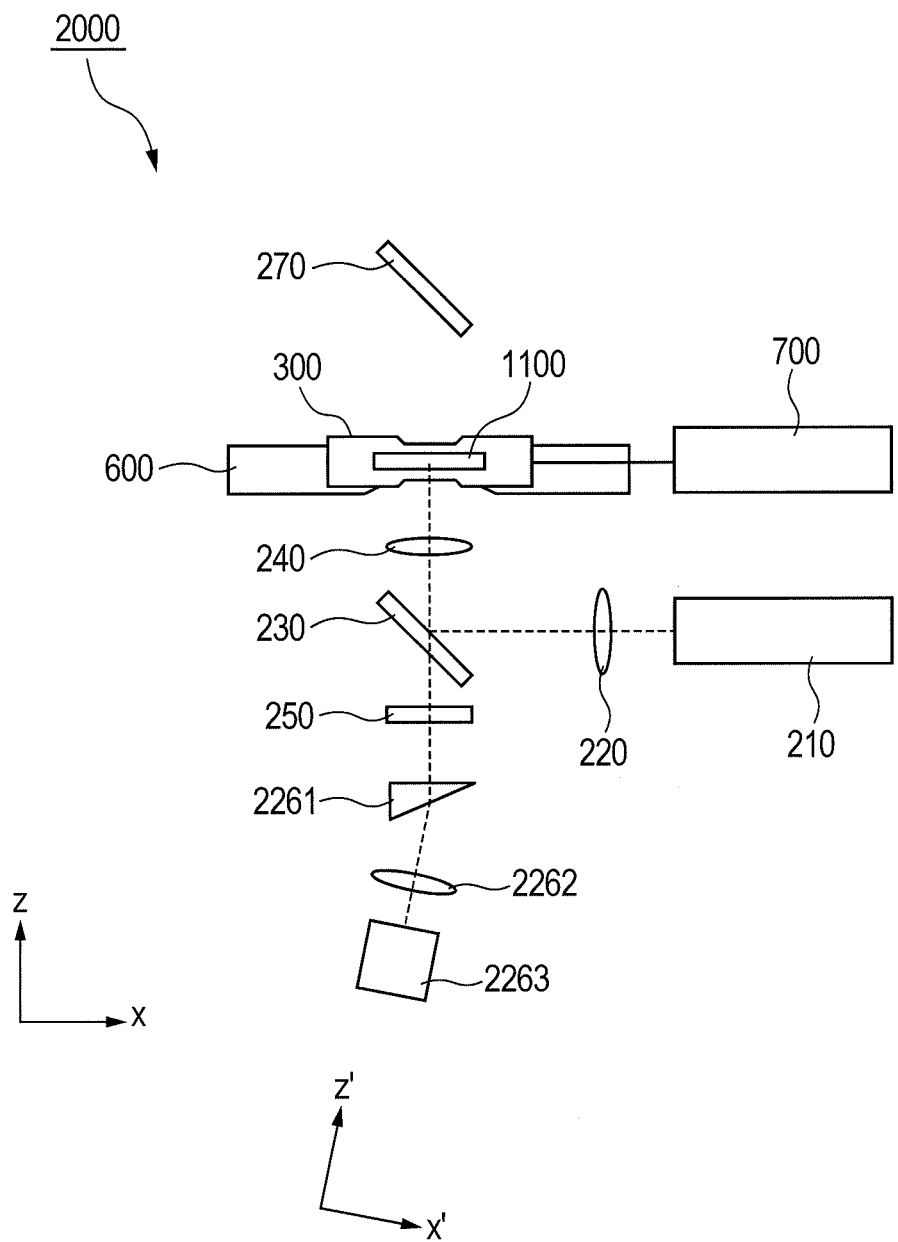
FIG. 12 is a schematic diagram of the construction of the biopolymer property analysis device using a multinanopore chip.

Next, one example of the construction of the biopolymer property analysis device according to this embodiment will be described referring to FIG. 12. FIG. 12 is a schematic diagram of the construction of the multianalysis device 2000 for analyzing the characteristics of the biopolymer according to the second embodiment. The multianalysis device 2000 is composed of the light source 210, the lens 220, the half mirror 230, the objective lens 240, the filter 250, a prism 2261, an image-formation lens 2262, a two-dimensional detector 2263, the terminator 270, the xyz high precision stage 600, the instrument for driving the sample 700, the sample cell 300, a measurement control device such as a personal computer (not indicated in the figure), or the like. The sample cell 300 houses the multinanopore chip 1100.

Next, the outline of the operational principle of this embodiment will be described below. The operational principle of the second embodiment is the same as that of the first embodiment with an exception that the multinanopore chip 1100 having a plurality of unit structures is used as a nanopore chip. Accordingly, the Raman scattered lights derived from the sample are generated in a plurality of points on the multinanopore chip 1100 individually. This Raman scattered light is condensed into the objective lens 240; passes through the half mirror 230; is caused to be diffracted with the prism 2261 after Rayleigh scattered light is removed by means of a filter; and forms an image on the detection surface of the two-dimensional detector 2263 using the image-formation lens 2262. The Rayleigh beam diffracted with the prism 2261 is refracted in the direction of the z' axis as shown in FIG. 12. The Rayleigh scattered lights from the opening of each of the unit structures on the multinanopore chip 1100 in the direction of the x axis and in the direction of the y axis form images on the two-dimensional detector 2263 in the direction of the x' axis and in the direction of the y' axis, respectively. Moreover, The Raman scattered light (Stokes line) is dispersed in the direction of the x' axis by means of the action of the prism 2261. The Raman scattered lights of the unit structures from the nanopores can be two-dimensionally expanded on the detection surface of the two-dimensional detector 2263, and obtained concurrently by adjusting wavelength dispersion spatially so that water Raman line (Storks line, Raman shift of about $-3000$ cm$^{-1}$) with relatively high intensity among Raman scattered lights cannot reach the Rayleigh line of the nanopore adjacent in the direction of the x' axis. Furthermore, the use of an additional bandpass filter in addition to the filter for removing the Rayleigh scattered light as a filter 250 allows undesired lights such as a water Raman line to be removed in advance and only the target Raman lines to be expanded two-dimensionally on the detection surface of the two-dimensional detector 2263 without overlapping, and obtained concurrently.

In this embodiment, a plurality of nanopores were arrayed regularly into a lattice pattern on the substrate 1100 in the direction of the x axis and in the direction of the y axis as shown in FIG. 11. The direction of the x axis, one of two directions, on the detection surface, was coincident with the direction of wavelength dispersion and one direction of the pixel array of the two-dimensional detector (x' direction). Furthermore, assuming that the interval between the arrays of the plurality of nanopores on the substrate 1100 in the x direction was dx and the interval in the y direction was dy, the relationship of the two figures was set to be dx≥dy. These individual conditions allow the pixels of the two-dimensional detector 2263 to be effectively used with no waste. In other words, the signals of Raman scattered lights from a larger number of nanopores can be obtained using the two-dimensional detector having the same size, improving the throughput of analysis.

It is required that since the position where the multinanopore chip 1100 is disposed along the central axis of the optical system may vary for each measurement, the relationship between pixel coordinates and wavelengths reeds to be calibrated, namely, wavelength calibration needs to be performed from the position of the detection surface for each nanopore every time. To solve this problem, the sample solution containing no target to be measured, namely the scattering spectrum of the reference solution was obtained prior to measurement of the Raman scattering spectrum of the polymer to be measured. Since the composition of the reference solution is known in advance, wavelength calibration can be performed for each nanopore based on the information for the composition. Giving an example, since the reference solution contains water, wavelength calibration was performed based on the wavelength dispersion per unit pixel using the detection pixel coordinates of water Raman scattered light or water Rayleigh scattered light. If a Rayleigh scattered light was blocked by the filter and not detected, the filter may be removed only during this process. This process allows the result of light detection obtained for each nanopore to be converted into the Raman scattering spectrum. In this case, subtraction of the scattering spectrum from the reference solution enables the net Raman scattering spectrum to be measured, achieving higher accuracy analysis. It should be noted that if the volume to be measured (near field volume) for each nanopore is equal to the volume across which the polymer to be measured, namely a lot of molecules in the reference solution are removed when the polymer to be measured enters the measured region, it is desirable that the aforementioned subtraction process is not performed or partially performed. The Raman scattering spectrum of the polymer to be measured may be obtained over the entire wavelength region, in which the spectrum can be obtained; however, the spectrum can be obtained only in the wavelength region necessary for base identification, namely only in the specific pixel region, to speed up the detection speed and reduce the amount of acquired data.

Generally, the DNA chain passes through the nanopore by means of electrophoresis at high speed. Giving an example, the single stranded DNA with base length of 10 kb (knt) passes through the nanopore in about 1 ms when 100 mV of voltage is applied, and the retention time (assuming that the spatial distribution of the near field is infinitely small) in the near field for each base is only 0.1 μs. Accordingly, to measure the signal of the Raman scattered light derived from each base in this condition independently, the operating speed of the two-dimensional detector 2263 needs to be set to the value higher than or equal to 1 MHz. When fluorescence, phosphorescence, scattered light, or the like are measured at high sensitivity under the conventional microscope system, in particular, when the targets to be measured, which are two-dimensionally distributed, are concurrently measured, the operating speed (frame rate) of the detector is generally set to a value lower than or equal to 30 Hz, in particular to a value lower than 1 KHz in case of high speed operation. Accordingly, the technique for setting the operating speed (frame rate) of the detector to the value higher than or equal to 1 KHz, preferably equal to 1 MHz remains a problem to be solved, which has been newly raised by the combination of the measurement of the nanopore and the measurement of the Raman scattering spectrum passing through it in the present invention. As the means for implementing such ultra-high speed detection, a CMOS (complementary metal oxide semiconductor) is preferably used rather than a CCD (charge-coupled device) generally used in the conventional microscopy system. When the CCD is used, AD conversion can be performed only on each detection element or an array of detection elements, while when CMOS is used, it can be performed concurrently on all the detection elements two-dimensionally-aligned, reducing the time required for AD conversion by several hundred-fold to several thousand-fold. Not limited to the CMOS, any of detectors having AD conversion function for each detection element may have the same effects. Alternatively, to reduce the time required for transferring a large volume of signals obtained at the detector to a control PC via a cable and board, and writing them in the built-in hard disk, or the like, it is effective that large-capacity memory is incorporated in the detector to store a large volume of signals therein without transferring via the aforementioned cable and board. On the other hand, with higher speed of detection, the exposure time is remarkably reduced in each measurement. To avoid deterioration in sensitivity due to this problem, the construction, in which a near field is introduced, a liquid-immersion type high-aperture objective lens is used, or any of high sensitivity elements such as an avalanche photodiode is used or an intensifier means, for example, an image intensifier is provided in the detector, or the like, is preferable for the present invention. In brief, in the present invention, the detector having a photointensifier means is preferably used. Moreover, in the present invention, the movements of the DNA chains passing through the individual nanopores are preferably caused to be synchronized with each other, more preferably the stopping time, during which the movements of the DNA chains in all the nanopores are stopped, is provided to measure the signals of the Raman scattered lights concurrently. Such a construction is effective in that the signals of the Raman scattered lights from the DNA chains in all the nanopores can be measured at high accuracy.

In the present invention, the prism 2261 was used as the wavelength dispersion means to obtain the Raman scattering spectrum, but to increase the resolution for wavelength dispersion, a diffraction grating can be used. This allows the types of the bases to be identified at higher accuracy.

It is possible to identify the bases based on the difference in the spectra of the Raman scattered lights without a wavelength dispersion means. Giving an example, it is also possible to obtain the 2-sectional image of the multinanopore using a dichroic mirror and extract the difference in the spectra of Raman scattered lights based on the intensity ratio between them. It is possible that the 3-sectional or 4-sectional image is obtained using a combination of a plurality of dichroic mirrors and the types of the bases are identified based on the intensity ratio between them at higher accuracy. This method has advantages over the method using wavelength dispersion in that with higher intensity of the signal for each pixel, the sensitivity is improved and a larger amount of nanopores can be measured concurrently using the two-dimensional detectors with the same dimensions.

The second embodiment is characterized in that it achieved high multiplicity in measurement and the high reliability of the obtained result because the spectra of the Raman scattered lights in a plurality of nanopores can be obtained concurrently. It is further characterized in that it provides high throughput in measurement at high multiplicity.

According to the variation of this embodiment, it is possible to dispose separate sample chambers for each nanopore and to measure different samples concurrently using the individual nanopores. The variation is further characterized in that it enables a plurality of samples to be measured in parallel, achieving high throughput.

Third Embodiment

Sandwich-Structured Nanopore Chip

Figure 13:
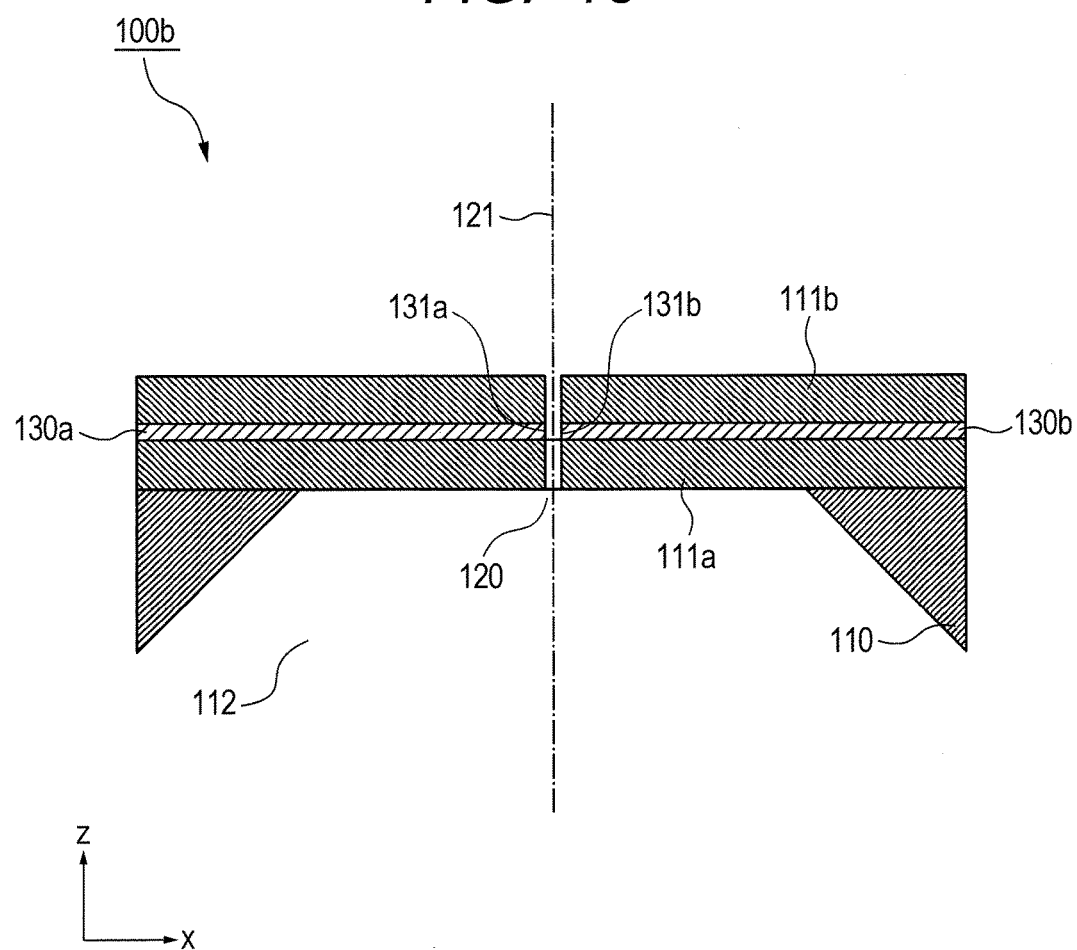
FIG. 13 is an enlarged schematic diagram of the cross section of the nanopore chip according to a third embodiment.

One example of the construction of the nanopore chip for analyzing the characteristics of the biopolymer of the present invention will be described referring to FIG. 13. FIG. 13 is an enlarged schematic diagram of the xz cross section of the nanopore 120 of the nanopore chip 100b containing the central axis. The substrate 110 has a thin film part 111a on the surface of the substrate in the upper part along the z axis, and electroconductive thin films 130a, 130b thereon, and further the thin film part 111b thereon. Other construction is the same as that of the variation of the first embodiment (FIG. 10).

A method for fabricating the nanopore chip 100b according to the third embodiment is similar to that according to the first embodiment (according to the variation of it) with exceptions that the patterns of the electroconductive thin films 130a, 130b were formed by electron beam lithography; the thin film part 111b was made of about 20 nm thickness of $SiO_2$ by sputtering; and then the nanopores were formed by TEM. The appearance of the nanopore chip 100b is similar to that according to the first embodiment (according to the variation of the first embodiment), as shown in FIG. 9 because the thin film part 111b is thin.

The operational principle of the third embodiment is the same as that according to the first embodiment (according to the variation of the first embodiment) with exceptions described below. First, since the electroconductive thin films 130a, 130b are sealed with the thin film part 111b, the near field, with which the sample can interact, is localized inside the nanopore 120. Since the remaining near field is sealed inside the thin films 111a and 111b, the near field cannot interact with the sample containing the biopolymer. For this reason, it is characterized in that no background signal is generated from the sample contained in other space than the space inside the target nanopore 120, achieving a high S/N ratio. In this embodiment, $SiO_2$ was used for the material of the thin film part 111b, which was formed by sputtering but the material for the thin film part 111b and the method for fabricating it are not limited those abovementioned. Various types of non-conductive materials can be used for the material of the thin film part 111b, which can be formed by an appropriate surface coating technique, achieving the same effects. Second, it is characterized in that since the near field is formed in the vicinity of the center of the nanopore 120 along the central axis thereof, the movement of the biopolymer, for example, DNA; namely the sample is limited by the nanopore in the xy direction. Accordingly, the sample can interact with the uniform near field, achieving high reproducibility of signals. Third, it is characterized in that since DNA is elongated along the axis during passing through the nanopore 120, the high-order conformation is denatured and the individual bases can be sequentially introduced into the near field, resulting in simplified relationship between the measurement region and the measurement time points, making analysis easier.

Fourth Embodiment

Nanopore Chip with Electroconductive Thin Films

Figure 14:
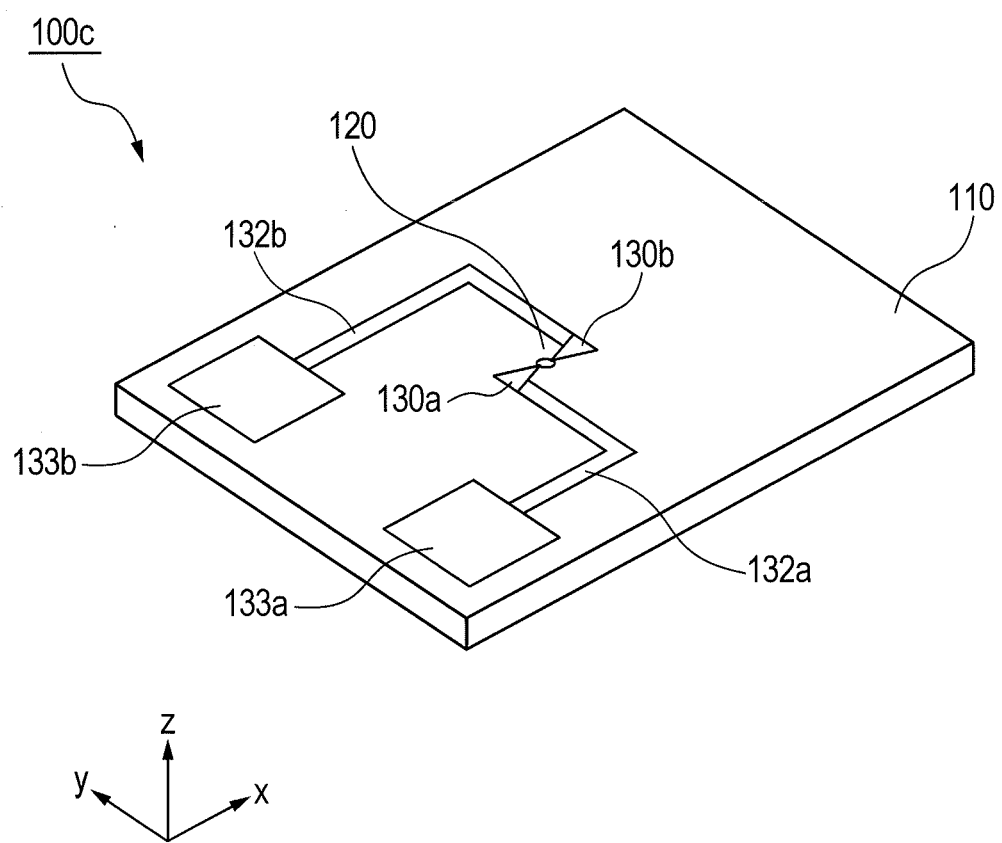
FIG. 14 is a schematic diagram of the nanopore diagram according to a fourth embodiment.

One example of the construction of the nanopore chip for analyzing the characteristics of the biopolymer of the present invention will be described referring to FIG. 14. FIG. 14 is a schematic diagram of the nanopore chip 100c for analyzing the characteristics of the biopolymer according to the fourth embodiment. As shown in the figure, the nanopore chip 100c is composed of the substrate 110, the nanopore 120, the electroconductive thin films 130a, 130b, the wiring patterns 132a, 132b, contacts 133a, 133b, or the like. The wiring patterns 132a, 132b, and the contacts 133a, 133b are electrically conducted with the electroconductive thin films 130a, 130b, respectively.

The wiring patterns 132a, 132b and the contacts 133a, 133b were formed in the same manner as that of the electroconductive thin films 130a, 130b according to the aforementioned embodiments with exceptions described below. In the fourth embodiment, gold was used for the material of the wiring patterns and the contacts, and the thickness of the wiring patterns was one micron and the thickness of the contacts was 100 microns.

The biopolymer property analysis device according to the fourth embodiment is the same as that according to the first to third embodiments with exceptions described below. In the fourth embodiment, the contacts 133a, 133b were coupled to a second voltage output of the instrument for driving the sample 700 via a card edge connector (not indicated in the figure) in opposite phase.

The operational principle of the fourth embodiment is the same as that according to the aforementioned embodiments with exceptions described below. In the fourth embodiment, the biopolymer was caused to pass through the nanopore 120 by means of electrophoresis by applying a pulsed voltage to the sample chambers from the instrument for driving the sample 700. Moreover, the near field was formed at the edges of the electroconductive thin films 130a, 130b by means of irradiation with a laser beam. When the pulsed voltage is not applied (OFF) from the instrument for driving the sample, electrophoresis voltage is released; the pulsed voltage in opposite phase (ON pulse) is applied to the contacts 133a, 133b; and this pulsed voltage is transferred to the electroconductive thin films 130a, 130b via the wiring patterns 132a, 132b and applied to the edges 131a, 131b (not indicated in the figure) thereof. Then, the phosphate group of DNA, namely a biopolymer, is drawn to the edges on the anode side of the electroconductive thin films 130a, 130b, during which DNA electrophoresis is temporarily stopped forcibly. During this period, the Raman scattering spectrum of the biopolymer is obtained. Similarly, when the ON pulse is applied from the instrument for driving the sample 700, an electrophoresis voltage is applied, while OFF pulse is applied to the contacts 133a, 133b in opposite phase to release temporal forced stoppage of DNA electrophoresis and resume DNA electrophoresis. During this period, the Raman scattering spectrum is not obtained.

The fourth embodiment is characterized in that the movement of the biopolymer through the nanopore can be controlled more accurately not only by driving a pulsed electrophoresis current but also by forcibly stopping or releasing the movement of the biopolymer by means of voltage application to the electroconductive thin films in synchronization with the pulsed electrophoresis current.

Fifth Embodiment

Nanopore Chip Using Graphene for Electroconductive Thin Films

Figure 15:
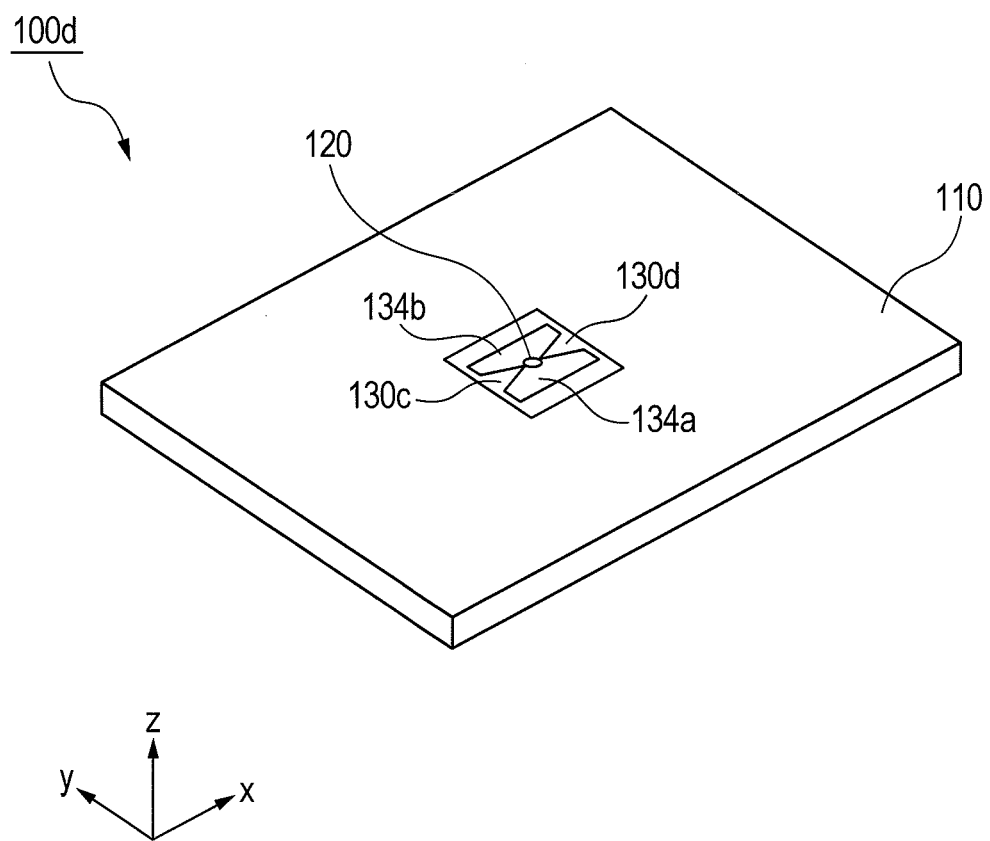
FIG. 15 is a schematic diagram of the nanopore chip according to a fifth embodiment.

One example of the construction of the nanopore chip for analyzing the characteristics of the biopolymer of the present invention will be described below referring to FIGS. 15 and 16. FIG. 15 is a schematic diagram of the nanopore chip 100d according to the fifth embodiment. The nanopore chip 100d is composed of the substrate 110, the nanopore 120, and the electroconductive thin films 130c, 130d, or the like. As shown in the figure, the fifth embodiment is similar to the third embodiment with main exceptions described below. First, a monolayer of graphite, namely graphene was used for the electroconductive thin films 130c, 130d. Second, the planar shapes of the electroconductive thin films 130c, 130d are coupled to each other such that a frame envelopes the outline of them. In other words, the electroconductive thin films 130c, 130d is formed into a single thin film structure (the voids 134a, 134b are also coupled to each other at the nanopore 120). Third, the diameter of the used nanopore 120 was 2 nm. The distance between the frame structure and the nanopore 120 was set to the distance equal to or slightly longer than the Distance Decay of Plasmon Coupling. Thus, plasmon generated in two electroconductive thin films 130c, 130d can be caused to reach sufficiently up to the vicinity of the nanopore by setting the lengths of the electroconductive thin films to the distance equal to the Distance Decay of Plasmon Coupling.

Figure 16:
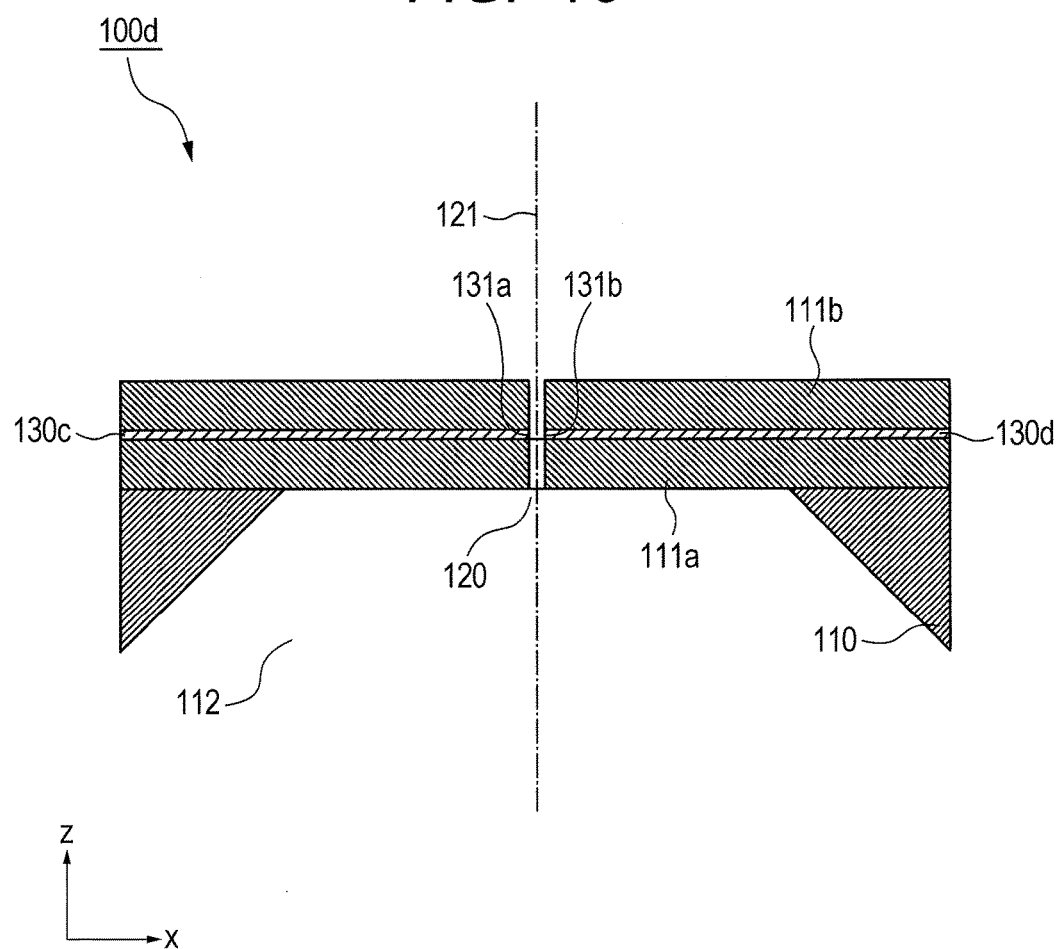
FIG. 16 is an enlarged schematic diagram of the cross section of the nanopore chip according to the fifth embodiment.

FIG. 16 is an enlarged schematic diagram of the xz cross section of the nanopore 120 containing the central axis thereof 121. Since the figure is highly magnified, the outer frames of the electroconductive thin films 130c, 130d are not shown in the figure.

The method for fabricating the nanopore chip 100d according to the fifth embodiment is similar to that according to the third embodiment with an exception that a step of forming the thin film part 111a on the substrate 110 was followed by a different step from the third embodiment. Specifically, graphene was separately made of graphite using a mechanical stripping technique and it was confirmed that it was a monolayer under the optical microscope. The graphene was transferred on a working support substrate using the wedging technique described in Schneider et al., Nano Letters (2010) 10, 1912. An electron beam was irradiated on the graphene on the entire support substrate using a high-intensity focused TEM (300 kV of accelerating voltage) to penetrate through the carbon layer and form the voids 134a, 134b and a coupling portion thereof. The support substrate was taken out from the TEM and the graphene processed in the aforementioned manner was transferred on the thin film part 111b of the substrate using the wedging technique again. Then, as with the third embodiment, the thin film part 111b was formed by sputtering and the nanopore 120 was formed using the TEM (by means of irradiation on the coupling portion of the voids 134a, 134b with electron beam). Thus, since the two electroconductive thin films 130c, 130d are formed into a shape connected to the frame, very small gaps between these films and complicated shapes such as the voids 134a, 134b can be easily formed at high reproducibility.

The operational principle of the fifth embodiment is the same as that according to the third embodiment with exceptions described below. First, since the electroconductive thin films 130c, 130d were made of graphene, the thickness thereof is very thin, about 0.3 nm. For this reason, it is characterized in that the thickness of the near field formed between the edges 131a, 131b of these films is also very thin, namely one to three DNA bases in length, achieving high spatial resolution. In other words, it is characterized in that since only fewer errors occur in analysis by the aforementioned difference method and the types of the bases can be identified at high accuracy. Second, since the electroconductive thin films 130c, 130d were made of graphene, the thickness of the edges 131a, 131b are very thin, and the edges 131a, 131b are sharply pointed in the direction of thickness. The near field is characterized in that with the sharply pointed tip thereof, the electric field concentrates thereon, enhancing intensifying effects. Third, it is characterized in that since the electroconductive thin films 130c, 130d were made of graphene (namely, carbon), stability is high against oxidization in the solution compared with silver. It should be noted that in this embodiment, a monolayer of graphene was used, but almost 2-layer to 15-layer graphene may be used. Since the very thin electroconductive thin films with thickness thinner than or equal to 5 nm can be formed even if these multilayer graphene or graphite is used, not only the same effects as those aforementioned can be achieved but also the specific effect of high intensity can be provided. Forth, it is characterized in that since the internal diameter of the nanopore is small, the speed at which the sample passes through can be suppressed.

According to a variation of the fifth embodiment, such a method can be used that the outer frame of the electroconductive thin films 130c, 130d are removed to separate the films and the wiring is drawn to connect to an external device as with the fourth embodiment. A measurement instrument for tunneling current can be used as the external device to measure tunneling current flowing through the sample between the edges 131a, 131b of the electroconductive thin films 130c, 130d. This variation is characterized in that since the thickness of the edges is thin, high spatial resolution can be achieved in measuring tunneling current. This variation can be combined with the first to the fifth embodiments to allow Raman measurement and tunneling current measurement to be performed concurrently. The complimentary use of the results of both measurements can improve the reliability of the obtained results. Alternatively, one of the results can be used to detect the DNA bases in synchronization with the timing of the other measurement to increase the S/N ratio in measurement, improving the reliability of the obtained results.

The nanopore chip with the electroconductive thin films disposed thereon of the present invention can be used in microfluorometry, for example, a nanopore sequencer using a fluorescent probe. In this case, the near field formed by the electroconductive thin films can be used to achieve high sensitivity and high spatial resolution.

Moreover, it is effective to combine two or more elements composing this invention aforementioned and the prior art in order to further improve the accuracy of analysis.

All cited publications, patents, and patent applications in the above description are incorporated herein by reference to the full text.

INDUSTRIAL APPLICABILITY

The present invention provides a biopolymer property analysis chip and property analysis device. The analysis chip and analysis device with high stability and high reliability of the present invention, which uses a solid state nanopore, is capable of analyzing two-dimensionally the characteristics of a biopolymer at high spatial resolution and high sensitivity. Thus, the present invention is useful in the fields, in which biopolymer property analysis is desired, for example, the biotechnology, biochemical, and medical fields.

LIST OF REFERENCE SIGNS 100, 100a, 100b, 100c, 100d nanopore chips
110 substrate
111, 111a thin film part of the substrate
111b thin film part
112 window on the substrate
120 nanopore
121 central axis of the nanopore
130, 130a, 130b, 130c, 130d electroconductive thin films
131, 131a, 131b edges of the electroconductive thin films
132a, 132b wiring patterns
133a, 133b contacts
134a, 134b voids
200 analysis device
210 light source
220 lens
230 half mirror
240 objective lens
250 filter
260 spectroscopic detector
270 terminator
300 sample cell
310 upper member
320 lower member
330 O-RING
410, 420, 430 sample flow channels
440 (lower) sample chamber
450 electrode chamber
460, 470 sample connection ports
480 (lower) electrode connection port
540 (upper) sample chamber
580 (upper) electrode connection port
600 xyz high precision stage
700 instrument for driving the sample
1100 multinanopore chip
1110 substrate
1120, 1121 nanopores
1130a, 1130b, 1131a, 1131b electroconductive thin films
2000 multianalysis device
2261 prism
2262 image-formation lens
2263 two-dimensional detector

The invention claimed is:

1. A biopolymer property analysis chip comprising:
a solid state substrate having a thin film made of an electric insulator material;
at least one nanopore formed in the solid state substrate; and
at least one electroconductive thin film disposed on the solid state substrate, wherein
the nanopore penetrates through the thickness of the thin film made of an electric insulator material,
the electroconductive thin film is disposed partially in contact with a circumference of the nanopore,
a biopolymer which has penetrated into the nanopore is caused to generate a Raman scattered light by irradiation with an external light, and
only a portion of the entire circumference of the nanopore has a plasmon resonance member structure,
the plasmon resonance member structure is an electroconductive thin film consisting of a single layer,
the plasmon resonance member structure is not in contact with another conductive material,
the electroconductive thin film is disposed in a middle depth of the nanopore along its central axis in the solid state substrate,
the thin film of the electric insulator material including a first film and a second film, and
the electroconductive thin film is sandwiched between the first film and the second film, such that a top surface and a bottom surface of the electroconductive thin film are not exposed.

2. The biopolymer property analysis chip defined in claim 1, wherein the external light is irradiated on the electroconductive thin film so as to generate a near field at an edge facing the opening of the nanopore, and the biopolymer which has penetrated into the nanopore is caused to generate a Raman scattered light.

3. The biopolymer property analysis chip defined in claim 1, wherein the electroconductive thin film has an acute-angled edge, the acute-angled edge being disposed facing the opening of the nanopore.

4. The biopolymer property analysis chip defined in claim 1, wherein at least the two electroconductive thin films are formed, at least the two electroconductive thin films being disposed so as to sandwich the opening of the nanopore facing each other.

5. The biopolymer property analysis chip defined in claim 1, wherein the electroconductive thin films are made of metal.

6. The biopolymer property analysis chip defined in claim 1, wherein the electroconductive thin films are made of graphite.

7. The biopolymer property analysis chip defined in claim 1, wherein the thickness of the electroconductive thin films is 0.1 nm to 10 nm.

8. The biopolymer analysis chip defined in claim 1, wherein the solid state substrate has a thin film part which substantially transmits light and the nanopore is formed on the thin film part.

9. The biopolymer property analysis chip defined in claim 1, wherein the electroconductive thin films are disposed on the surface of the solid state substrate.

10. The biopolymer property analysis chip defined in claim 1, wherein the depth of the nanopore is three times or more that of monomer units composing biopolymer.

11. The biopolymer property analysis chip defined in claim 1, wherein the biopolymer is selected from the group of nucleic acid, peptide nucleic acid, protein, sugar chain, and aptamer.

12. The biopolymer property analysis chip defined in claim 1, wherein the biopolymer property analysis is to determine the base sequence of nucleic acid.

13. A biopolymer property analysis device comprising:
the biopolymer property analysis chip defined in claim 1;
a light source; and
a one-dimensional or two-dimensional detector with frame rate of 1 kHz or more, wherein
external light is irradiated on the analysis chip from the light source, and a Raman scattered light from the biopolymer at the analysis chip is detected using the detector.

14. The biopolymer property analysis device defined in claim 13, further comprising frame buffer memory for recording the measured valued read out from the detector.

15. The biopolymer property analysis device defined in claim 13, further comprising a detector having a photointensifier part as the detector.

16. The biopolymer property analysis device defined in claim 13, further comprising a driving part configured to cause the monomers in a biopolymer to enter the nanopore one by one.

17. A method for analyzing the characteristics of a biopolymer comprising the steps of:
causing the biopolymer which has penetrated into the nanopore to generate a Raman scattered light by irradiation on a biopolymer property analysis chip defined in claim 1, with external light and
analyzing the characteristics of the biopolymer based on the Raman scattering spectrum.

18. The method for analyzing the characteristics of a biopolymer defined in claim 17, wherein the biopolymer is selected from the group of nucleic acid, peptide nucleic acid, protein, sugar chain, and aptamer.

19. The method for analyzing the characteristics of a biopolymer defined claim 17, wherein the base sequence of nucleic acid is determined.

20. The method for analyzing the characteristics of a biopolymer defined in claim 17, wherein the biopolymer is contained in a sample solution containing a second polymer, which cannot penetrate into the nanopore.

* * * * *